(12) United States Patent
Islam et al.

(10) Patent No.: US 10,351,488 B2
(45) Date of Patent: Jul. 16, 2019

(54) UNSATURATED POLYALPHA-OLEFIN MATERIALS

(71) Applicant: ExxonMobil Chemical Patents Inc., Baytown, TX (US)

(72) Inventors: Md Safatul Islam, Houston, TX (US); Patrick C. Chen, Houston, TX (US); Delanyo K. Seshie, Houston, TX (US); Sarah J. Mattler, League City, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 236 days.

(21) Appl. No.: 15/592,713

(22) Filed: May 11, 2017

(65) Prior Publication Data

US 2018/0037521 A1  Feb. 8, 2018

Related U.S. Application Data

(60) Provisional application No. 62/370,080, filed on Aug. 2, 2016.

(51) Int. Cl.
*C07C 2/32* (2006.01)
*C07C 2/34* (2006.01)

(52) U.S. Cl.
CPC .............. *C07C 2/32* (2013.01); *C07C 2/34* (2013.01); *C07C 2531/14* (2013.01); *C07C 2531/22* (2013.01)

(58) Field of Classification Search
CPC .... C07C 2531/14; C07C 2531/22; C07C 2/32
USPC .......................................................... 585/16
See application file for complete search history.

(56) References Cited

U.S. PATENT DOCUMENTS

| 4,827,064 | A | 5/1989 | Wu |
| 4,827,073 | A | 5/1989 | Wu |
| 4,914,254 | A | 4/1990 | Pelrine |
| 4,926,004 | A | 5/1990 | Pelrine et al. |
| 4,967,032 | A | 10/1990 | Ho et al. |
| 5,573,657 | A | 11/1996 | Degnan et al. |
| 5,688,887 | A | 11/1997 | Bagheri et al. |
| 5,705,577 | A | 1/1998 | Rossi et al. |
| 6,043,401 | A | 3/2000 | Bagheri et al. |
| 6,846,778 | B2 | 1/2005 | Johnson et al. |
| 6,858,767 | B1 | 2/2005 | Dimaio et al. |
| 7,019,091 | B2 | 3/2006 | Minami et al. |
| 7,053,254 | B2 | 5/2006 | Miller |
| 7,129,197 | B2 | 10/2006 | Song et al. |
| 7,241,375 | B2 | 7/2007 | Johnson et al. |
| 7,344,631 | B2 | 3/2008 | Bishop et al. |
| 7,589,145 | B2 | 9/2009 | Brant et al. |
| 7,795,194 | B2 | 9/2010 | Iimura et al. |
| 7,880,047 | B2 | 2/2011 | Knowles et al. |
| 8,071,687 | B2 | 12/2011 | Jiang et al. |
| 8,227,392 | B2 | 7/2012 | Wu et al. |
| 8,389,780 | B2 | 3/2013 | Knowles et al. |
| 8,530,712 | B2 | 9/2013 | Wu et al. |
| 8,748,361 | B2 | 6/2014 | Wu et al. |
| 8,816,034 | B2 | 8/2014 | Sato et al. |
| 9,409,834 | B2 | 8/2016 | Wu et al. |
| 9,796,645 | B2 * | 10/2017 | Emett ................. C08F 10/14 |
| 2005/0049373 | A1 | 3/2005 | Minami et al. |
| 2008/0042037 | A1 | 2/2008 | Orr |
| 2008/0177121 | A1 | 7/2008 | Wu et al. |
| 2009/0005279 | A1 | 1/2009 | Wu et al. |
| 2009/0036725 | A1 | 2/2009 | Wu et al. |
| 2009/0088355 | A1 | 4/2009 | Hee et al. |
| 2009/0247442 | A1 | 10/2009 | Hagemeister et al. |
| 2010/0087349 | A1 | 4/2010 | Lee et al. |
| 2010/0317904 | A1 | 12/2010 | Small et al. |
| 2010/0323937 | A1 | 12/2010 | Wu et al. |
| 2011/0040052 | A1 | 2/2011 | Bburton et al. |
| 2011/0082061 | A1 | 4/2011 | Carey et al. |
| 2011/0092752 | A1 | 4/2011 | Knowles et al. |
| 2011/0160502 | A1 | 6/2011 | Wu et al. |
| 2012/0302481 | A1 | 11/2012 | Katayama et al. |
| 2013/0023633 | A1 | 1/2013 | Holtcamp et al. |
| 2013/0090273 | A1 * | 4/2013 | Martin ............. C10M 169/04 508/150 |
| 2013/0245343 | A1 * | 9/2013 | Emett ................. C08F 210/04 585/18 |
| 2013/0303818 | A1 | 11/2013 | Inagaki et al. |
| 2014/0087986 | A1 | 3/2014 | Patil et al. |

(Continued)

FOREIGN PATENT DOCUMENTS

| EP | 1661921 | 5/2006 |
| EP | 1043341 | 10/2008 |

(Continued)

OTHER PUBLICATIONS

"Routes to Alpha-Olefins" Alpha Olefins Applications Handbook, Chapter 3, Edited by G. R. Lappin and J. D. Sauer, Marcel Dekker, Inc.,1989.
"Dispersants", Lubricant Additives: Chemistry and Application, Chapter 5, ed. By Leslie R. Rudnick, p. 143-170.
"Lubricant Base Oil Hydrogen Refining Processes" Lubricant Base Oil and Wax Processing, Chapter 6, by Avilino Sequeira, Jr., Marcel Dekker, Inc., NY, 1994, pp. 119-152.
"Industrial Technology of Next Generation Polymer by Metallocene Catalyst," (Reference A) title page, p. 993, and publication data (published May 20, 1995), and alleged partial translation provided by third party law firm, Enclosure 2, dated Oct. 4, 2012, Hoffmann EITLE, Patent-und Rechtsanwalte, 81925 Munchen, Arabellastr. 4.
"Living Polymerization by Homogeneous Transition Metal Catalyst," (Reference B) title page, pp. 46 and 47 and page with publication data (published on May 20, 1999), and alleged partial translation provided by third party law firm, Enclosure 3, dated Oct. 4, 2012, Hoffmann.cndot.EITLE, Patent-und Rechtsanwalte, 81925 Mu{umlaut over (n)}chen, Arabellastr. 4.

(Continued)

*Primary Examiner* — Ellen M McAvoy

(57) ABSTRACT

Unsaturated polyalpha-olefin (uPAO) materials comprising a mixture of vinylidene olefins, 1,2-di-substituted vinylene olefins, and tri-substituted vinylene olefins. The unsaturated PAO material can be made from alpha-olefin monomer(s) in the presence of a metallocene-compound-based catalyst system. The unsaturated PAO material can be used as intermediate material for making PAO materials having functional groups.

21 Claims, No Drawings

(56) References Cited

U.S. PATENT DOCUMENTS

| | | | |
|---|---|---|---|
| 2014/0135461 A1 | 5/2014 | Kohiruimaki et al. | |
| 2014/0235909 A1 | 8/2014 | Shimizu et al. | |
| 2014/0256997 A1 | 9/2014 | Shimizu et al. | |
| 2014/0309151 A1 | 10/2014 | Shimizu et al. | |
| 2015/0099679 A1 | 4/2015 | Yang et al. | |
| 2017/0051223 A1 | 2/2017 | Han | |
| 2018/0127332 A1* | 5/2018 | Kreischer | C07C 2/34 |

FOREIGN PATENT DOCUMENTS

| | | | |
|---|---|---|---|
| EP | 2738185 A | 6/2014 | |
| EP | 2746302 A | 6/2014 | |
| EP | 2470571 | 12/2014 | |
| JP | 2005200450 | 7/2005 | |
| JP | 5357605 | 4/2009 | |
| JP | 4283120 | 6/2009 | |
| JP | 2010/065072 | 3/2010 | |
| JP | 2010/070593 | 4/2010 | |
| JP | 5808292 | 6/2012 | |
| JP | 2013199517 | 10/2013 | |
| JP | 2013199585 | 10/2013 | |
| WO | 02/14384 A | 2/2002 | |
| WO | 2005/121280 A | 12/2005 | |
| WO | 2007/011459 | 1/2007 | |
| WO | 2008/042037 | 4/2008 | |
| WO | 2009/017953 | 2/2009 | |
| WO | 2009/123800 | 10/2009 | |
| WO | 2009/148685 A | 12/2009 | |
| WO | 2011/019541 A | 2/2011 | |
| WO | 2013055483 A | 4/2013 | |
| WO | 2014/065984 | 5/2014 | |
| WO | 2014/209712 | 12/2014 | |
| WO | 034659 A | 3/2017 | |

OTHER PUBLICATIONS

E. Riedel, Editor, Walter de Gruvter, Berlin, NY, 1999, Modem Inorganic Chemistry, Title page and pp. 696-697, alleged English translation provided by third party law firm. Hoffman EITLE Patent-und Rechtsanwalte, 81925 Munchen, Arabellastr 4.Enclosure 1dated Oct 4, 2012.

"New Polymer Produced by Metallocene Catalyst," (Reference C) title page, pp. 53-55 and page with publication data (published on Apr. 20, 1999), and alleged partial translation provided by third party law firm, Enclosure 4, dated Oct. 4, 2012, Hoffmann.cndot. EITLE, Patent-und Rechtsanwalte, 81925 Munchen, Arabellastr. 4.

M.M. Wu, Synthetic Lubricants and High Performance Functional Fluids, Marcel Dekker, book. Mar. 1999, pp. 195-213; Chapter 7. Alkylated Aromatics.

M. Sacchi et al., "Use of Different Alkoxysilanes as External Donors in MgClrSupported Ziegler-Hatta Catalysts to Obtain Propene/1-Butene Copolymers With Different Microstructure," Macromolecular Chemistry and Physics, 1994, vol. 195, pp. 2805-2816.

Ewen et al., "Stereoblock Isotactic-Hemiisotatctic Poly(propylene)s and Ethylene/Propylene Copolymers Obtained with ansa-Cyclopenta[1,2-b;4,3-b']dithiophene Catalysts", Macromolecular Chemistry and Physics (2004), 205, pp. 302-307.

Miller, S.A. "Insertion vs. site epimerization with singly-bridged and doubly-bridged metallocene polymerization catalysts", Journal of Organometallic Chemistry (2007), 692, pp. 4708-4716.

Z. Fan et al., "Effect of Ethoxy- and Methoxysilane Donors in Propene/1-Hexene Copolymerization With High-Yield Supported Ziegler-Hatta Catalysts," Macromolecular Chemistry and Physics, 1994, vol. 195, pp. 3889-3899.

Han, "Our mPAO platform is expanding: Introducing SpectraSyn EliteTM 300," 2016 China International Lubricants, Base Oils and Additives Conference, Langham Palace, Sep. 19, 2016.

* cited by examiner

UNSATURATED POLYALPHA-OLEFIN MATERIALS

PRIORITY

This application claims priority to and the benefit of U.S. Provisional Application No. 62/370,080, filed Aug. 2, 2016, and is incorporated by reference in its entirety.

FIELD OF THE INVENTION

The present disclosure relates to polyalpha-olefin ("PAO") materials. In particular, the present disclosure relates to ethylenically unsaturated PAO materials derived from polymerization of alpha-olefins.

BACKGROUND OF THE INVENTION

Oligomeric, ethylenically unsaturated molecules made from the polymerization of alpha-olefins are known. For example, U.S. Pat. No. 8,748,361 B2 discloses a mixture comprising unsaturated polyalpha-olefin ("uPAO") material made from, e.g., oligomerization of alpha-olefins in the presence of metallocene catalysts. It was disclosed in this reference that the uPAOs could comprise, among others, vinyls, vinylenes, 1,2-di-substituted vinylenes, and tri-substituted vinylenes. The vinyls and vinylidenes are terminal olefins, while the di- and tri-substituted vinylene olefins are internal olefins.

In U.S. Pat. No. 8,748,361 B2, mixtures of the uPAOs produced from the polymerization step were subsequently hydrogenated by hydrogen using a hydrogenation catalyst. A great majority of the C=C double bonds in the mixture were then hydrogenated to form a substantially saturated, stable, aliphatic PAO mixture which, in turn, can be separated by distillation to obtain a hydrogenated PAO material that is particularly suitable as the base stock for lubricating oil compositions used in various applications. To the extent the presence of C=C bonds in the PAO molecules in a lubricating oil composition is considered generally detrimental to the performance of the oil, especially to the oxidation stability thereof, it is highly desired that the uPAO has an overall composition that would result in saturation of the C=C bonds at a degree as high as possible in the hydrogenation step.

Recently, however, research and development in various chemical fields reveal that the ethylenically unsaturated PAO materials prepared from oligomerization of linear alpha-olefins can be particularly advantageously used as an intermediate for making various specialty chemicals because of the reactivity of the C=C double bond present in molecular structure of the oligomer molecules. For example, various chemical functional groups can be bonded to the carbon backbone of the unsaturated PAO molecule when a chemical agent reactive with the C=C bond is allowed to contact the unsaturated PAO material. The functional group thus introduced onto the PAO structure can bring about unique properties to the functionalized and saturated PAO molecules.

It has been found that the reactivity of the C=C bonds in vinyls, vinylidenes, 1,2-di-substituted vinylenes and tri-substituted vinylenes are different with regard to many chemical functionalization agents. For a specific type of functionalization agent, one or more particular type(s) of olefin(s) may be more desirable than the other(s). In addition, uPAOs having various molecular weight and molecular weight distribution and differing reactivities may be desired for making differing derivatives comprising differing functional groups thereon. Vinylidenes and tri-substituted vinylenes are more reactive than 1,2-di-substituted vinylenes with many common reagents reactive with C=C double bonds.

U.S. Publication No. 2013/0023633 A1 discloses metallocene compounds and use thereof in making polyolefins rich in vinyls.

There remains a need for unsaturated PAO materials particularly useful as intermediate materials for making functionalized PAOs.

SUMMARY OF THE INVENTION

It has been found that certain mixtures of unsaturated PAO molecules can be advantageously used as the intermediates for making PAO materials bearing functional groups thereon. Surprisingly, it has been found that unsaturated PAO materials having differing viscosity, molecular weight and compositions in terms of distribution of various types of olefins therein can be advantageously produced from similar monomers by using the same type of metallocene-compound-based catalyst system, making them suitable for use in fabricating differing functionalized derivatives for multiple, different uses.

Accordingly, a first aspect of the present invention relates to a polyalpha-olefin material comprising an olefin mixture of vinylidene olefins, 1,2-di-substituted vinylene olefins, and tri-substituted vinylene olefins. The olefin mixture have the following features: (I) an isotacticity of at least 50%, expressed as the mole percentage of (m,m)-triads as measured by using $^{13}C$ NMR; (II) a number-average molecular weight from 100 to 10,000; (III) a polydispersity index in the range from 1.0 to 2.0; (IV) a kinematic viscosity at 100° C. in the range from 20 to 1000 cSt; and (V) a concentration of the vinylidene olefins in the range from 3-80 mol %; a concentration of the 1,2-di-substituted vinylene olefins in the range from 10-70 mol %; and a concentration of the tri-substituted vinylene olefins in the range from 5-60 mol %, based on the total moles of the vinylidene olefins, 1,2-di-substituted vinylene olefins, and tri-substituted vinylene olefins.

DETAILED DESCRIPTION OF THE INVENTION

The term "alkyl" or "alkyl group" interchangeably refers to a saturated hydrocarbyl group consisting of carbon and hydrogen atoms. An alkyl group can be linear, branched linear, cyclic, or substituted cyclic.

The term "cycloalkyl" or "cycloalkyl group" interchangeably refers to a saturated to hydrocarbyl group wherein the carbon atoms form one or more ring structures.

The term "alkenyl" or "alkenyl group" interchangeably refers to a linear unsaturated hydrocarbyl group comprising a C=C bond therein.

The term "cycloalkenyl" or "cycloalkenyl group" interchangeably refers to cyclic hydrocarbyl group comprising a C=C bond in the ring.

The term "aryl" or "aryl group" interchangeably refers to a hydrocarbyl group comprising an aromatic ring structure therein.

The term "hydrocarbyl group" or "hydrocarbyl" interchangeably refers to a group consisting of hydrogen and carbon atoms only. A hydrocarbyl group can be saturated or unsaturated, linear or branched linear, cyclic or acyclic, aromatic or non-aromatic.

As used herein, a substituted group means such a group in which at least one atom is replaced by a different atom or a group. Thus a substituted alkyl group can be an alkyl group in which at least one hydrogen atom is replaced by a hydrocarbyl group, a halogen, any other non-hydrogen group, and/or a least one carbon atom and hydrogen atoms bonded thereto is replaced by a different group.

The term "Cn" group or compound refers to a group or a compound comprising carbon atoms at total number thereof of n. Thus, a "Cm-Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

The term "carbon backbone" refers to the longest straight carbon chain in the molecule of the compound or the group in question. "Branch" refers to any non-hydrogen group connected to the carbon backbone.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic. "Olefin" is intended to embrace all structural isomeric forms of olefins, unless it is specified to mean a single isomer or the context clearly indicates otherwise.

The term "alpha-olefin" refer to an olefin having a terminal carbon-to-carbon double bond in the structure thereof ($(R^1R^2)$—C=$CH_2$, where $R^1$ and $R^2$ can be independently hydrogen or any hydrocarbyl group, preferably $R^1$ is hydrogen, and $R^2$ is an alkyl group). A "linear alpha-olefin" is an alpha-olefin defined in this paragraph wherein $R^1$ is hydrogen, and $R^2$ is hydrogen or a linear alkyl group.

The term "vinyl" means an olefin having the following formula:

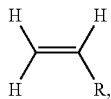

wherein R is a hydrocarbyl group, preferably a saturated hydrocarbyl group such as an alkyl group.

The term "vinylidene" means an olefin having the following formula:

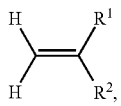

wherein $R^1$ and $R^2$ are each independently a hydrocarbyl group, preferably a saturated hydrocarbyl group such as alkyl group.

The term "1,2-di-substituted vinylene" means
(i) an olefin having the following formula:

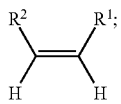

or
(ii) an olefin having the following formula:

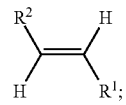

or
(iii) a mixture of (i) and (ii) at any proportion thereof,
wherein $R^1$ and $R^2$, the same or different at each occurrence, are each independently a hydrocarbyl group, preferably saturated hydrocarbyl group such as alkyl group.

The term "tri-substituted vinylene" means an olefin having the following formula:

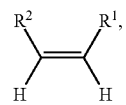

wherein $R^1$, $R^2$, and $R^3$ are each independently a hydrocarbyl group, preferably a saturated hydrocarbyl group such as alkyl group.

As used herein, "polyalpha-olefin(s)" ("PAO(s)") includes any oligomer(s) and polymer(s) of one or more alpha-olefin monomer(s). PAOs are oligomeric or polymeric molecules produced from the polymerization reactions of alpha-olefin monomer molecules in the presence of a catalyst system, optionally further hydrogenated to remove residual carbon-carbon double bonds therein. Thus, the PAO can be a dimer, a trimer, a tetramer, or any other oligomer or polymer comprising two or more structure units derived from one or more alpha-olefin monomer(s). The PAO molecule can be highly regio-regular, such that the bulk material exhibits an isotacticity, or a syndiotacticity when measured by $^{13}C$ NMR. The PAO molecule can be highly regio-irregular, such that the bulk material is substantially atactic when measured by $^{13}C$ NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO").

The term "pendant group" with respect to a PAO molecule refers to any group other than hydrogen attached to the carbon backbone other than those attached to the carbon atoms at the very ends of the carbon backbone.

The term "length" of a pendant group is defined as the total number of carbon atoms in the longest carbon chain in the pendant group, counting from the first carbon atom attached to the carbon backbone. The pendant group may contain a cyclic group or a portion thereof in the longest carbon chain, in which case half of the carbon atoms in the cyclic group are counted toward the length of the pendant group. Thus, by way of examples, a linear C8 pendant group has a length of 8; the pendant groups PG-1 (cyclohexylmethylene) and PG-2 (phenylmethylene) each has a length of 4; and the pendant groups PG-3 (o-heptyl-phenylmethylene) and PG-4 (p-heptylphenylmethylene) each has a length of 11. Where a PAO molecule contains multiple pendant groups, the arithmetic average of the lengths of all such pendant groups are calculated as the average length of the all pendant groups in the PAO molecule.

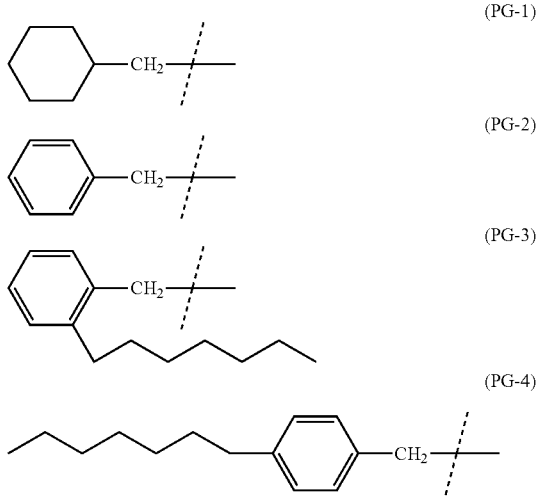

In the present disclosure, cyclopentadiene and cyclopentadienyl are abbreviated as Cp.

Unless specified otherwise, the term "substantially all" with respect to PAO molecules means at least 90 mol % (such as at least 95 mol %, at least 98 mol %, at least 99 mol %, or even 100 mol %).

Unless specified otherwise, the term "substantially free of" with respect to a particular component means the concentration of that component in the relevant composition is no greater than 10 mol % (such as no greater than 5 mol %, no greater than 3 mol %, or no greater than 1 mol %), based on the total quantity of the relevant composition.

As used herein, a "lubricant" refers to a substance that can be introduced between two or more moving surfaces and lower the level of friction between two adjacent surfaces moving relative to each other. A lubricant "base stock" is a material, typically a fluid at the operating temperature of the lubricant, used to formulate a lubricant by admixing it with other components. Non-limiting examples of base stocks suitable in lubricants include API Group I, Group II, Group III, Group IV, and Group V base stocks. Fluids derived from Fischer-Tropsch process or Gas-to-Liquid ("GTL") processes are examples of synthetic base stocks useful for making modern lubricants. GTL base stocks and processes for making them can be found in, e.g., WO 2005/121280 A1 and U.S. Pat. Nos. 7,344,631; 6,846,778; 7,241,375; 7,053,254.

All kinematic viscosity values in the present disclosure are as determined according to ASTM D445. Kinematic viscosity at 100° C. is reported herein as KV100, and kinematic viscosity at 40° C. is reported herein as KV40. Unit of all KV100 and KV40 values herein is cSt, unless otherwise specified.

All viscosity index ("VI") values in the present disclosure are as determined according to ASTM D2270.

All Noack volatility ("NV") values in the present disclosure are as determined according to ASTM D5800 unless specified otherwise. Unit of all NV values is wt %, unless otherwise specified.

All numerical values within the detailed description and the claims herein are modified by "about" or "approximately" the indicated value, and taking into account experimental error and variations that would be expected by a person having ordinary skill in the art.

In the present disclosure, all percentages of pendant groups, terminal carbon chains, and side chain groups are by mole, unless specified otherwise. Percent by mole is expressed as "mol %," and percent by weight is expressed as "wt %."

In the present disclosure, all molecular weight data are in the unit of g·mol$^{-1}$. Molecular weight of oligomer or polymer materials (including hydrogenated and unsaturated PAO materials) and distribution thereof in the present disclosure are measured by using gel permeation chromatography (GPC) equipped with a multiple-channel band filter based infrared detector ensemble IR5 (GPC-IR) with band region covering from 2700-3000 cm$^{-1}$ (all saturated C—H stretching vibration). Reagent grade 1,2,4-trichlorobenzene (TCB) (from Sigma-Aldrich) comprising 300 ppm antioxidant BHT is used as the mobile phase at a nominal flow rate of 1.0 mL/min and a nominal injection volume 200 μL. The whole system including transfer lines, columns, and detectors is contained in an oven maintained at 145° C. A given amount of sample is weighed and sealed in a standard vial with 10 μL flow marker (heptane) added thereto. After loading the vial in the auto-sampler, the oligomer or polymer is automatically dissolved in the instrument with 8 mL added TCB solvent at 160° C. with continuous shaking. The sample solution concentration is from 0.2 to 2.0 mg/ml, with lower concentrations used for higher molecular weight samples. The concentration, c, at each point in the chromatogram is calculated from the baseline-subtracted IR5 broadband signal, I, using the equation: $c=\alpha I$, where $\alpha$ is the mass constant determined with polyethylene or polypropylene standards. The mass recovery is calculated from the ratio of the integrated area of the concentration chromatography over elution volume and the injection mass which is equal to the pre-determined concentration multiplied by injection loop volume. The molecular weight is determined by combining universal calibration relationship with Mark-Houwink equation in which the M-H parameters a/K=0.695/0.00012 for mPAO. Number-average molecular weight (Mn) and weight-average molecular weight (Mw) of an oligomer or polymer are obtained from the above process. The polydispersity index (PDI) of the material is then calculated as follows:

PDI=Mw/Mn.

NMR spectroscopy provides key structural information about the synthesized polymers. Proton NMR (1H-NMR) analysis of the unsaturated PAO material gives a quantitative breakdown of the olefinic structure types (viz. vinyl, 1,2-di-substituted vinylene, tri-substituted vinylene, and vinylidene). In the present disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least 500 MHz is run under the following conditions: a 30° flip angle RF pulse, 120 scans, with a delay of 5 seconds between pulses; sample dissolved in CDCl$_3$ (deuterated chloroform); and signal collection temperature at 25° C. The following approach is taken in determining the concentrations of the various olefins among all of the olefins from an NMR spectrum. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, $C_i=100*Q_i/Q_t$).

TABLE I

| Type No. | Hydrogen Atoms Olefin Structure | Peak Region (ppm) | Peak Area | Number of Hydrogen Atoms | Quantity of Olefin (mol) | Concentration of Olefin (mol %) |
|---|---|---|---|---|---|---|
| T1 | $CH_2\!=\!CH\!-\!R^1$ | 4.95-5.10 | A1 | 2 | Q1 = A1/2 | C1 |
| T2 | $CH_2\!=\!CR^1R^2$ | 4.70-5.84 | A2 | 2 | Q2 = A2/2 | C2 |
| T3 | $CHR^1\!=\!CHR^2$ | 5.31-5.55 | A3 | 2 | Q3 = A3/2 | C3 |
| T4 | $CR^1R^2\!=\!CHR^3$ | 5.11-5.30 | A4 | 1 | Q4 = A4 | C4 |

Carbon-13 NMR ($^{13}$C-NMR) is used to determine tacticity of the PAOs of the present disclosure. Carbon-13 NMR can be used to determine the percentages of the triads, denoted (m,m)-triads (i.e., meso, meso), (m,r)- (i.e., meso, racemic) and (r,r)- (i.e., racemic, racemic) triads, respectively. The concentrations of these triads define whether the polymer is isotactic, atactic or syndiotactic. In the present disclosure, the percentage of the (m,m)-triads in mol % is recorded as the isotacticity of the PAO material. Spectra for a PAO sample are acquired in the following manner. Approximately 100-1000 mg of the PAO sample is dissolved in 2-3 ml of chloroform-d for $^{13}$C-NMR analysis. The samples are run with a 60 second delay and 90° pulse with at least 512 transients. The tacticity was calculated using the peak around 35 ppm ($CH_2$ peak next to the branch point). Analysis of the spectra is performed according to the paper by Kim, I.; Zhou, J.-M.; and Chung, H. Journal of Polymer Science: Part A: Polymer Chemistry 2000, 38 1687-1697. The calculation of tacticity is mm*100/(mm+mr+rr) for the molar percentages of (m,m)-triads, mr*100/(mm+mr+rr) for the molar percentages of (m,r)-triads, and rr*100/(mm+mr+rr) for the molar percentages of (r,r)-triads. The (m,m)-triads correspond to 35.5-34.55 ppm, the (m,r)-triads to 34.55-34.1 ppm, and the (r,r)-triads to 34.1-33.2 ppm.

I. The Unsaturated PAO Material

PAOs are oligomeric or polymeric molecules produced from the polymerization reactions of alpha-olefin monomer molecules in the presence of a catalyst system. An unsaturated PAO molecule in the material of the present disclosure contains a C=C bond therein. Each unsaturated PAO molecule has a carbon chain with the largest number of carbon atoms, which is designated the carbon backbone of the molecule. Any non-hydrogen group attached to the carbon backbone other than to the carbon atoms at the very ends thereof is defined as a pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical unsaturated PAO molecule can be represented by the following formula (F-1):

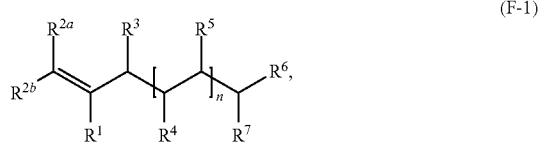

(F-1)

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl (preferably an alkyl) group, and n is a non-negative integer corresponding to the degree of polymerization. Where $R^1$, $R^{2a}$ and $R^{2b}$ are all hydrogen, (F-1) is a vinyl; where $R^1$ is not hydrogen, and both $R^{2a}$ and $R^{2b}$ are hydrogen, (F-1) is a vinylidene; and where $R^1$ is hydrogen, and only one of $R^{2a}$ and $R^{2b}$ is hydrogen, (F-1) is a di-substituted vinylene; and where $R^1$ is not hydrogen, and only one of $R^{2a}$ and $R^{2b}$ is hydrogen, then (F-1) represents a tri-substituted vinylene.

Where n=0, (F-1) represents an uPAO dimer produced from the reaction of two monomer molecules after a single addition reaction between two C=C bonds.

Where n=m, m being a positive integer, (F-1) represents a molecule produced from the reactions of m+2 monomer molecules after m+1 steps of addition reactions between two C=C bonds.

Thus, where n=1, (F-1) represents a trimer produced from the reactions of three monomer molecules after two steps of addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the unsaturated PAO material molecule (F-1). $R^2$, $R^3$, each of $R^4$ and $R^5$, and $R^6$, which can be substituted or unsubstituted hydrocarbyl (preferably alkyl) groups, are pendant groups (if not hydrogen).

If only alpha-olefin monomers are used in the polymerization process, and no isomerization of the monomers and oligomers ever occurs in the reaction system during polymerization, about half of $R^1$, $R^2$, $R^3$, all $R^4$ and $R^5$, $R^6$, and $R^7$ would be hydrogen, and one of $R^1$, $R^2$, $R^6$, and $R^7$ would be a methyl, and about half of groups $R^1$, $R^2$, $R^3$, all $R^4$ and $R^5$, $R^6$, and $R^7$ would be hydrocarbyl groups introduced from the alpha-olefin monomer molecules. In a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups ($R^2$, and all of $R^4$) would be 7.22 (i.e., (1+8*8)/9). This unsaturated PAO molecule, which can be produced by polymerizing 1-decene using certain metallocene catalyst systems described in greater detail below, can be represented by formula (F-2) below:

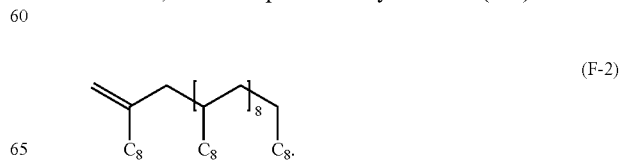

(F-2)

In this molecule, the longest 5%, 10%, 20%, 40%, 50%, and 100% of the pendant groups have average pendant group length of Lpg (5%) of 8, Lpg (10%) of 8, Lpg (20%) of 8, Lpg (50%) of 8, and Lpg (100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) unsaturated PAO molecule would comprise 34 carbon atoms, and the average pendant group length of the pendant groups ($R^2$, all $R^4$, and $R^5$) would be 3.67 (i.e., (1+1+7*8+1*8)/18). This unsaturated PAO molecule, which may be produced by polymerizing 1-decene using certain non-metallocene catalyst systems described in greater detail below, can be represented by the following formula (F-3):

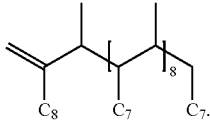

(F-3)

In this molecule, the longest 5%, 10%, 20%, 40%, 50%, and 100% of the pendant groups have average pendant group lengths of Lpg (5%) of 7, Lpg (10%) of 7, Lpg (20%) of 7, Lpg (50%) of 6.3, and Lpg (100%) of 3.67, respectively.

One skilled in the art, with knowledge of the molecular structure or the monomer used in the polymerization step for making the unsaturated PAO material, the process conditions (e.g., catalyst used, reaction conditions), and the polymerization reaction mechanism, can determine the molecular structure of the unsaturated PAO molecules, hence the pendant groups attached to the carbon backbone, and hence the Lpg (5%), Lpg (10%), Lpg (20%), Lpg (50%), and Lpg (100%), respectively.

Alternatively, one skilled in the art can determine the Lpg (5%), Lpg (10%), Lpg (20%), Lpg (50%), and Lpg (100%) values of a given unsaturated PAO material by using separation and characterization techniques available to polymer chemists. For example, gas chromatography/mass spectroscopy machines equipped with boiling point column separator can be used to separate and identify individual chemical species and fractions; and standard characterization methods such as NMR, IR, and UV spectroscopy can be used to further confirm the structures.

The unsaturated PAO materials of the present disclosure may be a homopolymer made from a single alpha-olefin monomer or a copolymer made from a combination of two or more alpha-olefin monomers.

Thus, the unsaturated PAO material of the present invention comprises a plurality of oligomeric and/or polymeric PAO molecules, which may be the same or different. Each unsaturated PAO molecule comprises a plurality of pendant groups, which may be the same or different, and the longest 5%, 10%, 20%, 40%, 50%, and 100% of the pendant groups of all of the olefin molecules of the unsaturated PAO material have an average pendent group length of Lpg (5%), Lpg (10%), Lpg (20%), Lpg (40%), Lpg (50%), and Lpg (100%), respectively. It is preferred that at least one of the following conditions is met:

$$a1 \leq Lpg\ (5\%) \leq a2, \quad (i)$$

where a1 and a2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0 15.5, 16.0, as long as a1<a2;

$$b1 \leq Lpg\ (10\%) \leq b2, \quad (ii)$$

where b1 and b2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as b1<b2;

$$c1 \leq Lpg\ (20\%) \leq c2, \quad (iii)$$

where c1 and c2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as c1<c2;

$$d1 \leq Lpg\ (40\%) \leq d2; \quad (iv)$$

where d1 and d2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as d1<d2;

$$e1 \leq Lpg\ (50\%) \leq e2; \quad (v)$$

where e1 and e2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, as long as e1<e2; and $$f1 \leq Lpg\ (100\%) \leq f2, \quad (vi)$$

where f1 and f2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, as long as f1<f2.

Preferably, at least 60% of the pendent groups on olefin molecules in the unsaturated PAO material are straight chain alkyls having at least 4 (or at least 6, or at least 8, or at least 10, or at least 12) carbon atoms. Preferably, at least 90% of the pendent groups on the olefin molecules in the unsaturated PAO material are straight chain alkyls having at least 4 (or at least 6, or at least 8, or at least 10, or at least 12) carbon atoms.

The unsaturated PAO material of the present disclosure may have various levels of regio-regularity. For example, each unsaturated PAO molecule may be substantially atactic, isotactic, or syndiotactic. The unsaturated PAO material, however, can be a mixture of different molecules, each of which can be atactic, isotactic, or syndiotactic. Without intending to be bound by a particular theory, however, it is believed that regio-regular unsaturated PAO molecules, especially the isotactic ones, due to the regular distribution of the pendant groups on substantially the same side of the carbon backbone, especially the longer ones, tend to allow for higher reactivity of the C=C bonds, and therefore are preferred as intermediates for making functionalized PAO materials. Thus, it is preferred that at least 50%, or 60%, or 70%, or 80%, or 90%, or even 95%, by mole, of the olefin molecules in the unsaturated PAO material are regio-regular. It is further preferred that at least 50%, or 60%, or 70%, or 80%, or 90%, or even 95%, by mole, of the olefin molecules in the unsaturated PAO material are isotactic. As discussed above, unsaturated PAO materials made by using metallocene catalysts can have such high regio-regularity (syndiotacticity or isotacticity), and therefore are preferred. For example, it is known that a metallocene-based catalyst system can be used to make unsaturated PAO molecules with over 50%, 60%, 70%, 75%, 80%, 85%, 90%, 95%, or even substantially 100% isotacticity.

The unsaturated PAO material of the present disclosure can have various viscosity. For example, it may have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt. The exact viscosity of the unsaturated PAO material can be controlled by, e.g., monomer used, polymerization temperature, polymerization reactor residence time, catalyst used, concentration of catalyst used, distillation and separation conditions, and mixing multiple unsaturated PAO materials with different viscosity.

The unsaturated PAO material of the present disclosure comprises a mixture of three or more different types of olefins: vinylidene olefins at a concentration of [a], 1,2-di-substituted vinylene olefins at a concentration of [b], and tri-substituted vinylene olefins at a concentration of [c], respectively, expressed as the mole percentages thereof based on the total moles of all three categories of olefins. For a given unsaturated PAO material of the present disclosure, the concentrations [a], [b], and [c] can independently vary in a range regardless of the viscosity of the mixture of the vinylidene and vinylene olefins. However, in general, the concentrations of 1,2-substituted vinylenes ([b]) and tri-substituted vinylenes ([c]) tend to increase with the kinematic viscosity at 100° C. (KV100) of the olefin mixture, and the concentration of the vinylidenes ([a]) tends to decrease with the KV100, if the olefin mixtures at differing KV100 are made from the same monomer(s), by using the same catalyst (such as the same metallocene-compound-based catalyst system). Without intending to be bound by a particular theory, it is believed that this is due to the differing chain termination mechanisms and/or isomerization from vinylidenes to vinylenes that occur in the polymerization step or subsequent treatment steps when high-KV100 uPAO is produced.

The concentrations [a], [b], and [c] of the various categories of olefins in the uPAO of the present disclosure are within these ranges: $3 \leq [a] \leq 80$; $10 \leq [b] \leq 70$; and $5 \leq [c] \leq 60$.

Preferably, [a], [b], and [c] are within the following ranges:

$$a1 \leq [a] \leq a2, \text{ preferably } a3 \leq [a] \leq a4;$$

$$b1 \leq [b] \leq b2; \text{ preferably } b3 \leq [b] \leq b4; \text{ and}$$

$$c1 \leq [c] \leq c2, \text{ preferably } c3 \leq [c] \leq c4;$$

where:
a1=−0.06*V+26.9, a3=−0.09*V+55.2;
a2=−0.06*V+83.9, a4=−0.08*V+76.8;
b1=0.04*V+12.9, b3=0.09*V+14.4;
b2=0.12*V+29.1, b4=0.09*V+23.4;
c1=0.01*V+7.6, c3=0.01*V+11.1;
c2=−0.04*V+62.1, and c4=−0.02*V+30.3;
where V in the above equations is KV100 of the olefin mixture.

Preferably, in a first olefin mixture in the unsaturated PAO material of the present disclosure having a KV100 in the range from 30 to 100 cSt, the following conditions are met: a1=46; a2=75; b1=17; b2=33; c1=11; and c2=30. In this relatively low-viscosity olefin mixture, vinylidenes constitute a great majority of the olefins. In making functionalized PAOs from this olefin mixture, one can use a functionalizing agent having a high reactivity toward the vinylidenes, but a lower reactivity toward the vinylenes.

Preferably, in a second olefin mixture in the unsaturated PAO material of the present disclosure having a KV100 in the range from 120 to 180 cSt, the following conditions are met: a1=39; a2=67; b1=25; b2=40; c1=12; and c2=28. This medium-viscosity olefin mixture typically has a lower vinylidene concentration and higher vinylene concentrations than the first olefin mixture above. To functionalize the vinylenes, one can choose an agent reactive with the vinylenes, or conduct the functionalization in the presence of a catalyst capable of activating the vinylene C=C bonds.

Preferably, in an olefin mixture in the unsaturated PAO material of the present disclosure having a KV100 in the range from 270 to 330 cSt, the following conditions are met: a1=25; a2=55; b1=38; b2=53; c1=14; and c2=25. This high-viscosity olefin mixture typically has an even lower vinylidene concentration and higher vinylene concentrations than the second olefin mixture above. To functionalize the vinylenes in this olefin mixture, one can likewise choose an agent reactive with the vinylenes, or conduct the functionalization in the presence of a catalyst capable of activating the vinylene C=C bonds.

Desirably, the vinylidene and vinylene olefin mixtures in the unsaturated PAO material of the present disclosure have an isotacticity of at least 50 mol % (or at least 55, 60, 65, 70, 75, 80, 85, or even 90 mol %), expressed in terms of the molar percentages of the (m,m)-triads among all the triads among all of the olefin molecules. As discussed above, such high isotacticity can be achieved by using specific metallocene-compound-based catalyst system, and is desirable because of the high degree of exposure of the C=C bond of the vinylidenes (and to a lesser degree, the 1,2-di-substituted and tri-substituted vinylenes) in those molecules where a great majority of the pendant groups are distributed on one side of the carbon backbone of the unsaturated PAO molecules.

In addition, the vinylidene and vinylene olefins in unsaturated PAO materials of the present disclosure advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8). A narrow molecular weight distribution of the unsaturated PAO molecules can be achieved by using metallocene-compound-based catalyst systems in the polymerization step under controlled polymerization conditions (temperature fluctuation, residence time, and the like). Such narrow PDI is desirable in that it defines a material with a high degree of homogeneity in molecular weight, molecular size, rheology behavior, viscosity index, and degrading behavior (such as shear stability and oxidation stability). From an olefin mixture with such degree of homogeneity one can produce a functionalized material having a similar degree of homogeneity as well.

In general, the olefin mixture in the unsaturated PAO material of the present disclosure can have an average molecular weight that varies widely (and correspondingly, a KV100 that varies widely). Typically, the olefin mixture has a number average molecular weight of Mw, where Mw1≤Mw≤Mw2, where Mw1 and Mw2 can be, independently, 100, 200, 300, 400, 500, 600, 700, 800, 900, 1000, 2000, 3000, 4000, 5000, 6000, 7000, 8,000, 9000, 10,000, 20,000, 30,000, 40,000, or even 50,000, as long as Mw1<Mw2.

The unsaturated PAO material of the present disclosure may further comprise, in addition to the vinylidenes and vinylenes described above, vinyls. However, in general, the latter, if found present, is typically present at a very low concentration, such as no greater than 5 mol % (or no greater than 4, 3, 2, 1, 0.5, 0.3, or even 0.1 mol %) based on the total moles of all olefins in the unsaturated PAO material.

The unsaturated PAO material of the present disclosure may comprise, in addition to the olefin mixture, saturated hydrocarbons. The saturated hydrocarbons may be produced in-situ in the polymerization step of the alpha-olefin for making the uPAO, e.g., where the polymerization is conducted in the presence of a hydrogen-containing atmosphere. Alternatively or additionally, the saturated hydrocarbons may be produced by a partial hydrogenation of a portion of the uPAO as produced from the polymerization step. Still alternatively or additionally, the saturated hydrocarbon may be blended with an olefin mixture to obtain a mixture of desired property and composition. Nonetheless, it is desired that the unsaturated PAO material of the present disclosure comprises vinylidenes, tri-substituted vinylenes, 1,2-disubstituted vinylenes and optional vinyls olefins at a total concentration thereof of at least 50 wt % (or at least 60, 65, 70, 75, 80, 85, 90, 92, 94, 95, 96, 97, 98, or 99 wt %) based on the total weight of the unsaturated PAO material.

In general, it is desired that the unsaturated PAO material of the present disclosure has a bromine number in a range from Nb(PAO)1 to Nb(PAO)2, where Nb(PAO)1 and Nb(PAO)2 can be, independently, 1.0, 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. Desirably, a great majority, such as at least 80, 85, 90, 95, 98, or even 99 mol % of the molecules in the unsaturated PAO material of the present disclosure is unsaturated. Desirably, each unsaturated PAO molecule is capable of addition reaction with one $Br_2$ molecule to obtain a 1,2-dibromo-derivative thereof.

Molecular structures of exemplary vinylidene uPAOs made from a mixture of 1-octene and 1-dodecene alpha-olefin monomers at a molar ratio of 4:1 can be schematically represented by formula (F-V) as follows, where n can be any integer.

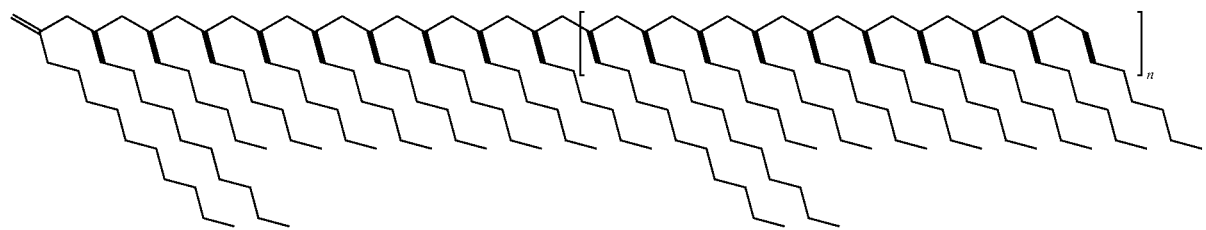

The two C10 pendant groups are shown to be next to each other. In real molecules, they may be randomly distributed among all of the pendant groups. The structure shows nearly 100% isotacticity, i.e., 100 mol % of (m,m)-triads in the structure. In real molecules, a small fraction may be (m,r)- or (r,r)-triads. Nonetheless, each of the long pendant groups can extend to form a substantially linear chain, and interact with other long straight carbon chains from other unsaturated PAO molecules and other molecules in its vicinity.

Because of the presence of the C=C bonds in the unsaturated PAO molecules, when exposed to $O_2$ molecules (such as when exposed to air), the unsaturated PAO material can be oxidized if not protected by a more reactive material toward $O_2$. To that end, in the unsaturated PAO material, anti-oxidant materials may be added to prolong its shelf life and facilitate handling, storage, and transportation thereof. Such anti-oxidants can include, but are not limited to, those anti-oxidants typically used in lubricant base stocks and lubricating oil compositions. Non-limiting examples of such anti-oxidants and the use quantity thereof are given in paragraphs [0101]-[0108], pages 9 and 10 of U.S. Patent Application Publication No. 2010/0087349 A1, the content of which is incorporated by reference in its entirety.

II. Use of the Unsaturated PAO Material of the Present Disclosure

The unsaturated PAO material of the present disclosure as described above, desirably produced by polymerization of alpha-olefin monomers in the presence of a metallocene-compound-based catalyst system, can be advantageously used as a chemical intermediate for making many products, especially those comprising a PAO molecule moiety and one or more functional groups. The hydrocarbon molecules in the unsaturated PAO material, if prepared from the polymerization of alpha-olefin monomers containing only one C=C double bond in their molecules, tend to comprise no more than one C=C bond each, with the rest of its structure consisting of C—C bonds and C—H bonds.

For example, one can subject the unsaturated PAO material of the present disclosure to a step of hydrogenation by contacting it with a hydrogen-containing atmosphere in the presence of a hydrogenation catalyst, such as one containing one or more of Fe, Co, Ni, precious metals (such as Ru, Rh, Pd, Os, Ir, Pt), and the like. Because of the composition of the unsaturated PAO material of the present disclosure, they can be advantageously hydrogenated to convert a great majority of the C=C bonds present in the olefin molecules into carbon-carbon single bonds, thereby achieving a material that is substantially aliphatic and saturated characterized by a low Bromine number of no greater than 5.0, preferably no greater than 4.0, more preferably no greater than 3.0, most preferably no greater than 2.0. Such hydrogenated, largely aliphatic hydrocarbon materials have high viscosity index, low pour point, high oxidation stability and high shear stability. They are advantageously used as, e.g., base stocks for lubricant compositions, such as those used in internal combustion engines, automotive grease oils, industrial grease oils, gear box oils, and the like.

As mentioned above, the C=C bonds present in the molecules of the unsaturated PAO material of the present disclosure are highly reactive, and therefore can react with multiple, different types of chemical agents having useful functional groups, thereby creating a PAO molecule further comprising a functional group bonded thereto. The functional group can comprise, in turn, other functional groups, which can react with additional chemical agents, bringing additional or different functional groups to the final molecule. The hydrocarbon substrate (i.e., the PAO structure) of thus functionalized PAO can impart desired properties to the functionalized material, such as solubility in organic media or hydrophobicity, and the functional groups can impart other desired properties to the final material, such as polarity, hydrophilicity (thus, solubility in aqueous media), and the like, making the final material particularly useful where such dual properties are desired (e.g., detergents).

U.S. Publication No. 2014/0087986 A1 discloses multiple methods for making functionalized PAO from unsaturated PAO materials produced by polymerization of alpha-olefin monomers in the presence of a metallocene-compound-based catalyst system. The entirety of the disclosure of this reference is incorporated herein.

It is highly desired that upon functionalization of the unsaturated PAO material, the C=C double bond in the reacted unsaturated PAO molecule becomes saturated (i.e., each carbon atom in the original C=C bond is then bonded to four atoms). This can be achieved by using functionalization agents reactive substantially only toward the C=C bonds, but substantially inert toward the C—C bonds and C—H bonds in the uPAO olefin molecules under the functionalization conditions. Given that each uPAO olefin molecule comprises typically only one C=C bond, the uPAO olefin molecule would then become saturated upon such functionalization reaction.

Upon functionalization of the C=C bond in the uPAO olefin molecule, the overall structure of the functionalized PAO molecule would be substantially similar to that of a hydrogenated PAO molecule where the C=C bond has been saturated by hydrogenation as described above. Assuming that the bond between the functional group(s) to the carbon atom(s) is not significantly less robust than the C—C and C—H bonds, and assuming the functional group(s) per se are not significantly less robust than a pendant group on the PAO molecule under the use conditions, one can expect a stable oligomeric/polymeric structure retaining at least some of the interesting and useful properties of a saturated PAO molecule, such as one or more of viscosity index, oxidation stability, shear stability, Bromine number, and the like. The retained properties can make the functionalized PAO material particularly useful in applications typical for the saturated PAO materials, such as lubricating oil compositions, and the like.

It is highly desirable that the functionalization agent used to functionalize the unsaturated PAO material is highly selective toward reacting with the C=C bond only, and is substantially inert with respect to the C—C bonds and C—H bonds on the unsaturated PAO molecules. This can ensure the production of functionalized PAO molecules each comprising one or two functional group(s) only, and a complete functionalization of substantially all of the unsaturated PAO molecules if desired. In applications such as lubricating oil compositions, because of the high reactivity of C=C bonds in the unsaturated PAO molecules, it may be desired that substantially all of the C=C bonds in the unsaturated PAO molecules are saturated before the functionalized PAO material is put into the oil compositions, either as a base stock or as an additive.

Additionally and alternatively, one may also functionalize the unsaturated PAO molecules by substituting one or more of the hydrogen atoms on the carbon backbone or one of the pendant groups with a functional group by using chemical agents known to be reactive with C—H bonds. Because a unsaturated PAO molecule typically comprise many C—H bonds at multiple locations, such reaction would be less selective than selective functionalization of C=C bonds by using a functionalization agent that is inert to the C—H bonds, and can result in very large number of very different molecules, and thus is less desirable than functionalization selective toward the C=C bonds only.

III. Hydrogenated PAO Material

The unsaturated PAO material made by the method of the present disclosure can be directly used as a lubricating oil base stock and other applications because it can be made to have the desired physical properties, particularly rheological properties interesting for such applications. However, due to the presence of a C=C bonds on a large portion, if not all, of the unsaturated PAO molecules, direct use thereof as a lubricating oil base stock can cause stability issues to the oil if the oil is exposed to an oxidative environment, such as the air. Thus, in general, for lubricating oil applications, it is highly desirable that the unsaturated PAO material is hydrogenated to remove at least a portion, preferably a major portion of the C=C bonds in the PAO molecules. Hydrogenation can be performed by contacting the unsaturated PAO material of the present disclosure with a hydrogen-containing atmosphere in the presence of a hydrogenation catalyst, such as a transition-metal-based catalyst. Metals such as Fe, Co, Ni, precious metals (Ru, Rh, Pd, Re, Os, Ir, Pt) are known to be catalytically active for hydrogenating olefins and therefore can be used for catalyzing the hydrogenation of the unsaturated PAO material of the present disclosure to make a substantially hydrogenated, aliphatic, and saturated PAO material. Such hydrogenated PAO material can be characterized by a low bromine number of no greater than 5.0, preferably no greater than 4.0, more preferably no greater than 3.0, most preferably no greater than 2.0. Such hydrogenated, largely aliphatic hydrocarbon materials have high viscosity index, low pour point, high oxidation stability and high shear stability.

The hydrogenated PAO material made from hydrogenating the unsaturated PAO material will have viscosity, molecular weight distribution, pendent group distribution, polydispersity index, that are very similar to those of the precursor unsaturated PAO material.

Thus, the hydrogenated PAO material of the present disclosure can have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt.

The hydrogenated PAO material of the present disclosure advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8. Such narrow PDI is desirable in that it defines a material with a high degree of homogeneity in molecular weight, molecular size, rheology behavior, viscosity index, and degrading behavior (such as shear stability and oxidation stability).

The hydrogenated PAO material of the present disclosure can have a number average molecular weight of Mw, where $Mw1 \le Mw \le Mw2$, and Mw1 and Mw2 can be, independently, 100, 200, 300, 400, 500, 600, 700, 800, 900, 1000, 2000, 3000, 4000, 5000, 6000, 7000, 8,000, 9000, 10,000, 20,000, 30,000, 40,000, or even 50,000, as long as $Mw1 < Mw2$.

The hydrogenated PAO can be used as a high-quality API Group IV base stock. Various grades of the hydrogenated mPAO with KV100 varying from very low such as 1 cSt to very high such as 5,000 cSt can be made by using the method of the present disclosure, and used for blending with each other and other API Group I, II, III, IV, or V base stocks to make high-quality lubricating oil formulations, such as internal combustion engine oils, automobile drive line oils, industrial oils, greases, and the like. Furthermore, the mPAO can be used as heat transfer oil (e.g., transformer oil), processing oil, hydraulic power transfer oil, and the like.

IV. The Catalyst System

IV.1 the Metallocene Compound

The unsaturated PAO material of the present disclosure is typically made by polymerization of alpha-olefin (preferably linear alpha-olefin) feed in the presence of a catalyst system comprising a metallocene compound, an activator, and optionally a scavenger. Many metallocene compounds known to one having ordinary skill in the art can be used. For example, many of the metallocene compounds disclosed in U.S. Pat. No. 9,409,834 B2 can be used for making the unsaturated PAO materials of the present disclosure, the relevant portions thereof are incorporated herein by reference. Particularly useful examples of metallocene compounds for making the unsaturated PAO material of the present disclosure have a structure of (MC-I) or (MC-II) below:

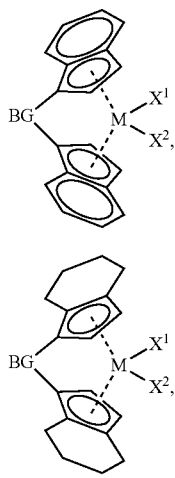

where M is Hf or Zr, $X^1$ and $X^2$, same or different, are independently selected from halogens and C1-C50 substituted or unsubstituted linear, branched, or cyclic hydrocarbyl groups, and -BG- is a bridging group selected from

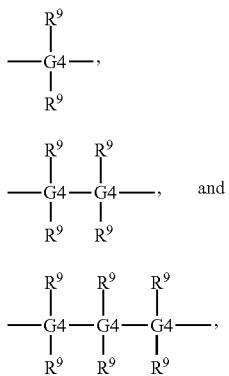

where groups G4 are, the same or different at each occurrence, independently selected from carbon, silicon, and germanium, and each $R^9$ is independently a C1-C30 substituted or unsubstituted linear, branched, or cyclic hydrocarbyl groups. Preferred $R^9$ includes substituted or unsubstituted methyl, ethyl, n-propyl, phenyl, and benzyl. Preferably -BG- is category (i) or (ii) above. More preferably -BG- is category (i) above. Preferably all $R^9$'s are identical. Preferably G4 is silicon, and all $R^9$ groups are methyl.

IV.2 Activators and Activation of the Metallocene Compound

The metallocene compounds, when activated by a commonly known activator such as non-coordinating anion activator, form active catalysts for the polymerization or oligomerization of olefins. Activators that may be used include Lewis acid activators such as triphenylboron, tris-perfluorophenylboron, tris-perfluorophenylaluminum and the like and or ionic activators such as dimethylanilinium tetrakisperfluorophenylborate, triphenylcarboniumtetrakis perfluorophenylborate, dimethylaniliniumtetrakisperfluorophenylaluminate, and the like.

A co-activator is a compound capable of alkylating the transition metal complex, such that when used in combination with an activator, an active catalyst is formed. Co-activators include alumoxanes such as methylalumoxane, modified alumoxanes such as modified methylalumoxane, and aluminum alkyls such trimethylaluminum, triisobutyl-aluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

U.S. Pat. No. 9,409,834 B2 (line 39, column 21 to line 44, column 26) provides a detailed description of the activators and co-activators that may be used with the metallocene compound in the catalyst system of the present disclosure. The relevant portions of this patent are incorporated herein by reference in their entirety.

Additional information of activators and co-activators that may be used with the metallocene compounds in the catalyst system of the present disclosure can be found in U.S. Patent Application Publication No. 2013/0023633 A1 (paragraph [0178], page 16 to paragraph [0214], page 22). The relevant portions of this reference is incorporated herein by reference in their entirety.

IV.3 Scavenger

A scavenger is a compound that is typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 B2, line 37, column 33 to line 61, column 34 provides detailed description of scavengers useful in the process of the present disclosure for making PAO. The relevant portions in this patent on scavengers, their identities, quantity, and manner of use are incorporated herein in their entirety.

V. The Process for Making PAO

The process for making PAO of the present disclosure broadly includes a step of contacting an alpha-olefin, such as a C4-C30 alpha-olefin feed with a catalyst system comprising a metallocene compound described above in a polymerization reactor under polymerization conditions to effect a polymerization reaction to obtain a polymerization reaction mixture comprising vinylidenes, tri-substituted vinylenes, 1,2-di-substituted vinylenes, and optionally vinyls; and obtaining an unsaturated PAO material from the polymerization reaction mixture, wherein the unsaturated PAO material comprises vinylidenes, tri-substituted vinylenes, 1,2-di-substituted vinylenes, and optionally vinyls.

V.1 the Monomer(s)

The alpha-olefin feed for making the PAO materials of the present disclosure may comprise one or more of C2-C32 alpha-olefins. Thus, the feed may comprise ethylene, propylene, C4 alpha-olefins, and C5 alpha-olefins. Preferably ethylene, propylene, C4 alpha-olefins (1-butene and 2-methyl-1-propene), and C5 alpha-olefins (1-pentene and various isomers of methyl-1-butene) is supplied to the polymerization reactor, each independently at no higher than c1 mol %, based on the total moles of the alpha-olefins supplied to the polymerization reactor, where c1 can be 50, 40, 30, 20, 10, 5, 4, 3, 2, 1, 0.5, 0.1, 0.01, for each of them. Preferably, the alpha-olefin feed is substantially free of ethylene, propylene, C4 alpha-olefins, and C5 alpha-olefins.

Preferably, the feed comprises (i) C2 and C3 alpha-olefins combined, or (ii) C2, C3, and C4 alpha-olefins combined, or (iii) C2, C3, C4, and C5 alpha-olefins combined, at a quantity of no higher than c2 mol %, based on the total moles of the alpha-olefins supplied to the polymerization reactor, where c2 can be 50, 40, 30, 20, 10, 5, 4, 3, 2, 1, 0.5, 0.1, 0.01. Preferably, the alpha-olefin feed is substantially free of (i) C2 and C3 alpha-olefins combined, or (ii) C2, C3, and C4 alpha-olefins combined, or (iii) C2, C3, C4, and C5 alpha-olefins combined.

The feed may preferably comprise one or more of C4-C32 (preferably C6-C24, more preferably C6-C18, still more preferably C8-C18) alpha-olefins. Preferably substantially all alpha-olefins in the feed are C4-C32 (more preferably C6-C24, more preferably C6-C18, still more preferably C8-C18) alpha-olefins. "Substantially all" means at least 90 mol % (or at least: 92 mol %, 94 mol %, 95 mol %, 96 mol %, 98 mol %, 99%, or even 99.5 mol %), based on the total moles of the alpha-olefins present in the feed.

Preferably, at least a portion (e.g., at least: 80 mol %, 85 mol %, 90 mol %, 95 mol %, 96 mol %, 98 mol %, even 99 mol %, or even 99.5 mol %) of the alpha-olefins present in the feed are linear alpha-olefins (LAOs), i.e., those without a branch attached to the carbon backbone thereof. Examples of preferred LAOs are 1-butene, 1-pentene, 1-hexene, 1-heptene, 1-octene, 1-nonene, 1-decene, 1-dodecene, 1-tetradecene, 1-hexadecene, 1-octadecene, 1-icocene, C22, C24, C26, C28, C30, and C32 LAOS. PAO materials made from such LAOs by using the process of the present disclosure tend to have fewer branches and pendant groups, leading to more uniform PAO molecular structures, hence better performance for applications such as lubricant base stocks, lubricant additives, and the like.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer tends to have pendant groups attached to the carbon backbone with highly uniform length.

In certain situations, a mixture of two, three, or even more alpha-olefins in the feed is desired to produce a copolymer PAO material. To that end, alpha-olefins with the following combinations are particularly advantageous: C6/C8, C6/C10, C6/C12, C6/C14, C6/C16, C8/C10, C8/C12, C8/C14, C8/C16, C10/C12, C10/C14, C10/C16, C10/C18, C12/C14, C12/C16, C12/C18, C12/C20, C6/C8/C10, C6/C8/C12, C6/C8/C14, C6/C10/C12, C6/C10/C14, C8/C10/C12, C8/C10/C14, C8/C12/C14, C10/C12/C16, C10/C12/C18, C10/C14/C16, C10/C14/C18, and the like. Desirably, at least one of the alpha-olefins in the mixture feed is an LAO. More desirably, substantially all of the alpha-olefins in the mixture feed are LAOS.

Preferred alpha-olefin monomers are mono-olefins containing one C=C bond per monomer molecule, though those olefins containing two or more C=C bonds per monomer molecule can be used as well.

The alpha-olefins used herein can be produced directly from ethylene growth process as practiced by several commercial production processes, or they can be produced from Fischer-Tropsch hydrocarbon synthesis from CO/$H_2$ syngas, or from metathesis of internal olefins with ethylene, or from cracking of petroleum or Fischer-Tropsch synthetic wax at high temperature, or any other alpha-olefin synthesis routes. A preferred feed for this invention is preferably at least 80 wt % alpha-olefin (preferably linear alpha olefin), preferably at least 90 wt % alpha-olefin (preferably linear alpha olefin), more preferably 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components have diluent effects and are believed to not have a substantial detrimental effect on the polymerization of alpha-olefins. In other words, the process described herein can selectively convert alpha-olefins in a mixture and leave the other components unreacted. This is particularly useful when ethylene is not present in the mixture. This technology can be used to separate out alpha-olefins from a mixture by selectively reacting them with polymerization or oligomerization catalyst systems completely eliminating the need to separate alpha-olefins from the remainder of the components in a mixed feed stream. This is economically advantageous, for example, in a process utilizing Fisher-Tropsch synthesis olefin product streams containing alpha-olefins, internal-olefins and branched olefins. Such a mixture can be fed to the oligomerization technology as described herein and to selectively react away the alpha-olefin. No separate step to isolate the alpha-olefin is needed. Another example of the utility of this process involves alpha-olefins produced by the metathesis of internal olefins with ethylene, which may contain some internal olefins. This mixed olefin base stock feed can be reacted as is in the polymerization/oligomerization process of the present disclosure, which selectively converts the alpha-olefins into lube products. Thus, one can use the alpha-olefin for the base stock synthesis without having to separate the alpha-olefin from internal olefin. This can bring a significant improvement in process economics. The feed olefins can be the mixture of olefins produced from other linear alpha-olefin process containing C4 to C20 alpha-olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

V.2 Feed Purification

Olefin feed and or solvents may be treated to remove catalyst poisons, such as peroxides, oxygen or nitrogen-containing organic compounds or acetylenic compounds before being supplied to the polymerization reactor. The treatment of the linear alpha-olefin with an activated 13 Angstrom molecular sieve and a de-oxygenate catalyst, i.e., a reduced copper catalyst, can increase catalyst productivity (expressed in terms of quantity of PAO produced per micromole of the metallocene compound used) more than 10-fold. Alternatively, the feed olefins and or solvents are treated with an activated molecular sieve, such as 3 Angstrom, 4 Angstrom, 8 Angstrom or 13 Angstrom molecular sieve, and/or in combination with an activated alumina or an activated de-oxygenated catalyst. Such treatment can desirably increase catalyst productivity 2- to 10-fold or more.

V.3 Polymerization Reaction

Many polymerization/oligomerization processes and reactor types used for metallocene-catalyzed polymerization or oligomerization such as solution, slurry, and bulk polymerization or oligomerization processed can be used for making the unsaturated PAO material of the present disclosure. If a solid or supported catalyst is used, a slurry or continuous fixed bed or plug flow process is suitable. Preferably, the monomers are contacted with the metallocene compound and the activator in the solution phase, bulk phase, or slurry phase, preferably in a continuous stirred tank reactor or a continuous tubular reactor. Preferably, the temperature in any reactor used herein is from −10° C. to 250° C., preferably from 30° C. to 220° C., preferably from 50° C. to 180° C., preferably from 60° C. to 170° C. Preferably, the pressure in any reactor used herein is from 0.1 to 100 atmospheres, preferably from 0.5 to 75 atmospheres, preferably from 1 to 50 atmospheres. Alternatively, the pressure is any reactor used herein is from 1 to 50,000 atmospheres, preferably 1 to 25,000 atmospheres. Alternatively, the monomer(s), metallocene and activator are contacted for a residence time of 1 second to 100 hours, preferably 30 seconds to 50 hours, preferably 2 minutes to 6 hours, preferably 1 minute to 4 hours. Alternatively, solvent or diluent is present in the reactor and is preferably selected from the group consisting of butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, mixed xylenes, ethylbenzene, isopropylbenzene, and n-butylbenzene; preferably toluene and or xylenes and or ethylbenzene, normal paraffins (such as Norpar solvents available for ExxonMobil Chemical Company in Houston, Tex.), or isoparaffin solvents (such as Isopar® solvents available for ExxonMobil Chemical Company in Houston, Tex.). These solvents or diluents are usually pre-treated in same manners as the feed olefins.

Typically, in the processes of this invention, one or more metallocene compounds, one or more activators, and one or more monomers are contacted to produce polymer or oligomer. These catalysts may be supported and as such will be particularly useful in the known slurry, solution, or bulk operating modes conducted in single, series, or parallel reactors. If the catalyst, activator or co-activator is a soluble compound, the reaction can be carried out in a solution mode. Even if one of the components is not completely soluble in the reaction medium or in the feed solution, either at the beginning of the reaction or during or at the later stages of the reaction, a solution or slurry type operation is still applicable. In any instance, the catalyst system components, dissolved or suspended insolvents, such as toluene or other conveniently available aromatic solvents, or in aliphatic solvent, or in the feed alpha-olefin stream, are fed into the reactor under inert atmosphere (usually nitrogen or argon blanketed atmosphere) to allow the polymerization or oligomerization to take place. The polymerization or oligomerization can be run in a batch mode, where all the components are added into a reactor and allowed to react to a pre-designed degree of conversion, either to partial conversion or full conversion. Subsequently, the catalyst is deactivated by any possible means, such as exposure to air or water, or by addition of alcohols or solvents containing deactivating agents. The polymerization or oligomerization can also be carried out in a semi-continuous operation, where feeds and catalyst system components are continuously and simultaneously added to the reactor so as to maintain a constant ratio of catalyst system components to feed olefin(s). When all feeds and catalyst system components are added, the reaction is allowed to proceed to a pre-determined stage. The reaction is then discontinued by catalyst deactivation in the same manner as described for batch operation. The polymerization or oligomerization can also be carried out in a continuous operation, where feeds and catalyst system components are continuously and simultaneously added to the reactor so to maintain a constant ratio of catalyst system and feed olefins. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. Preferably, any of the processes to prepare PAO's described herein are continuous processes. Preferably, the continuous process comprises the steps of a) continuously introducing a feed stream comprising at least 10 mol % of the one or more C5 to C24 alpha-olefins into a reactor, b) continuously introducing the metallocene compound and the activator into the reactor, and c) continuously withdrawing the polyalphaolefin from the reactor. Alternatively, the continuous process comprises the step of maintaining a partial pressure of hydrogen in the reactor of 200 psi (1379 kPa) or less, based upon the total pressure of the reactor, preferably 150 psi (1034 kPa) or less, preferably 100 psi (690 kPa) or less, preferably 50 psi (345 kPa) or less, preferably 25 psi (173 kPa) or less, preferably 10 psi (69 kPa) or less. Alternately, the hydrogen, if present, is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less. Alternately, the hydrogen, if present, is present in the feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Preferred reactors range in size from 2 ml and up. Usually, it is preferable to use reactors larger than one liter in volume for commercial production. The production facility may have one single reactor or several reactors arranged in series or in parallel or in both to maximize productivity, product properties and general process efficiency. The reactors and associated equipment are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds.

One or more reactors in series or in parallel may be used in the present disclosure. The metallocene compound, activator and when required, co-activator, may be delivered as a solution or slurry in a solvent or in the alpha-olefin feed stream, either separately to the reactor, activated in-line just prior to the reactor, or preactivated and pumped as an activated solution or slurry to the reactor. Polymerizations/ oligomerization are carried out in either single reactor operation, in which monomer, or several monomers, catalyst/activator/co-activator, optional scavenger, and optional modifiers are added continuously to a single reactor or in series reactor operation, in which the above components are added to each of two or more reactors connected in series. The catalyst system components can be added to the first reactor in the series. The catalyst system component may also be added to both reactors, with one component being added to first reaction and another component to other reactors. Preferably, the metallocene compound is activated in the reactor in the presence of olefin. Alternatively, the metallocene compound such as the dichloride form of the metallocene compounds is pre-treated with alkylaluminum reagents, especially, triisobutylaluminum, tri-n-hexylaluminum and/or tri-n-octylaluminum, followed by charging into the reactor containing other catalyst system component and the feed olefins, or followed by pre-activation with the other catalyst system component to give the fully activated catalyst, which is then fed into the reactor containing feed olefins. In another alternative, the pre-catalyst metallocene is mixed with the activator and/or the co-activator and this activated catalyst is then charged into reactor, together with feed olefin stream containing some scavenger or co-activator. In another alternative, the whole or part of the co-activator is pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection allows polymer or oligomer blend preparation under conditions analogous to those using individual catalysts. Polymers having increased MWD are available from polymers made with mixed catalyst systems and can thus be achieved. Mixed catalyst can comprise two or more metallocene compounds and or two or more activators.

Preferably ethylene is present in the feed at 10 mol % or less, preferably 0.5 to 8 moles %, preferably 0.5 to 5 mol %, preferably from 1 to 3 mol %.

The PAO's described herein can also be produced in homogeneous solution processes. Generally this involves polymerization or oligomerization in a continuous reactor in which the polymer formed and the starting monomer and catalyst materials supplied, are agitated to reduce or avoid concentration or temperature gradients. Temperature control in the reactor is generally obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers or solvent) or combinations of the above. Adiabatic reactors with pre-chilled feeds may also be used. The reactor temperature depends on the catalyst used and the product desired. Higher temperatures tend to give lower molecular weights and lower temperatures tend to give higher molecular weights, however this is not a hard and fast rule. In general, the reactor temperature preferably can vary between about 0° C. and about 300° C., more preferably from about 10° C. to about 230° C., and most preferably from about 25° C. to about 200° C. Usually, it is important to control the reaction temperature as pre-determined. In order to produce fluids with narrow molecular distribution, such as to promote the highest possible shear stability, it is useful to control the reaction temperature to obtain minimum of temperature fluctuation in the reactor or over the course of the reaction time. If multiple reactors are used in series or in parallel, it is useful to keep the temperature constant in a pre-determined value to minimize any broadening of molecular weight distribution. In order to produce fluids with broad molecular weight distribution, one can adjust the reaction temperature swing or fluctuation, or as in series operation, the second reactor temperature is preferably higher than the first reactor temperature. In parallel reactor operation, the temperatures of the two reactors are independent. Or, one can use two types of metallocene catalysts.

The pressure in any reactor used herein can vary from about 0.1 atmosphere to 100 atmosphere (1.5 psi to 1500 psi), preferably from 0.5 bar to 75 atm (8 psi-1125 psi), most preferably from 1.0 to 50 atm (15 psi to 750 psi). The reaction can be carried out under the atmosphere of nitrogen or with some hydrogen. Sometimes a small amount of hydrogen is added to the reactor to improve the catalyst. The amount of hydrogen is preferred to keep at such a level to improve catalyst productivity, but not induce any hydrogenation of olefins, especially the feed alpha-olefins because the conversion of alpha-olefins into saturated paraffins is very detrimental to the efficiency of the process. The amount of hydrogen partial pressure is preferred to be kept low, less than 50 psi, preferably less than 25 psi, preferably less than 10 psi, preferably less than 5 psi. Preferably, the concentration of hydrogen in the reactant phase is less than 10,000 ppm, 100 ppm, preferably less than 50 ppm, preferably less than 10 ppm. In a particularly preferred embodiment in any of the process described herein the concentration of hydrogen in the reactor is kept at a partial pressure of preferably 50 psi (345 kPa) or less, preferably 10 psi (69 kPa) or less. Alternately, in any process described herein hydrogen, if present, is present in the reactor and or feed at 10,000 ppm or less, preferably 1000 ppm or less by weight, preferably 750 ppm or less, preferably 500 ppm or less, preferably 250 ppm or less, preferably 100 ppm or less, preferably 50 ppm or less, preferably 25 ppm or less.

The reaction time or reactor residence time can depend on the catalyst used, the amount of catalyst used, and the desired conversion level. Different metallocene compounds have different activities. Usually, a higher degree of alkyl substitution on the Cp ring, or bridging improves catalyst productivity. High amount of catalyst loading tends to gives high conversion at short reaction time. However, high amount of catalyst usage make the production process uneconomical and difficult to manage the reaction heat or to control the reaction temperature. Therefore, it is useful to choose a catalyst with maximum catalyst productivity to minimize the amount of metallocene and the amount of activators needed. When the catalyst system is metallocene plus methylalumoxane, the range of methylalumoxane used can be in the range of 0.1 milligram (mg) to 500 mg/g of alpha-olefin feed. A more preferred range is from 0.05 mg to 10 mg/g of alpha-olefin feed. Furthermore, the molar ratios of the aluminum to metallocene (Al/M molar ration) can range from 2 to 4000, preferably 10 to 2000, more preferably 50 to 1000, preferably 100 to 500. When the catalyst system is metallocene plus a Lewis Acid or an ionic promoter with NCA component, the metallocene use can be in the range of 0.01 microgram to 500 micrograms of metallocene component/gram of alpha-olefin feed. A preferred range is from 0.1 microgram to 100 microgram of metallocene component per gram of alpha-olefin feed. Furthermore, the molar ratio of the NCA activator to metallocene can be in the range from 0.1 to 10, preferably 0.5 to 5, preferably 0.5 to 3. If a co-activator of alkylaluminum compound is used, the molar ratio of the Al to metallocene can be in the range from 1 to 1000, preferably 2 to 500, preferably 4 to 400.

Typically, one prefers to have the highest possible conversion (close to 100%) of feed alpha-olefin in shortest possible reaction time. However, in CSTR operation, sometimes it is beneficial to run the reaction at an optimum conversion, which can be less than 100% conversion, but preferably close to 100%. There are also occasions, when partial conversion is more desirable when the narrowest possible PDI of the product is desirable because partial conversion can avoid a PDI broadening effect. If the reaction is conducted to less than 100% conversion of the alpha-olefin, the unreacted starting material after separation from other product and solvents/diluents can be recycled to increase the total process efficiency.

Desirable residence times for any process described herein are in the range from 1 minute to 20 hours, typically 5 minutes to 10 hours.

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers or oligomers. Hydrocarbon solvents both aliphatic and aromatic are suitable. Aromatics such as toluene, xylenes, ethylbenzene, propylbenzene, cumene, t-butylbenzene are suitable. Alkanes, such as hexane, heptane, pentane, isopentane, and octane, Norpar® or Isopar® solvents from ExxonMobil Chemical Company in Houston, Tex. are also suitable. Generally, toluene is most suitable to dissolve catalyst system components. Norpar®, Isopar® solvent or hexanes are preferred as reaction diluents. Oftentimes, a mixture of toluene and Norpar® or Isopar® is used as diluent or solvent.

The process can be carried out in a continuous stirred tank reactor or plug flow reactor, or more than one reactor operated in series or parallel. These reactors may have or may not have internal cooling and the monomer feed may or may not be refrigerated. See the general disclosure of U.S. Pat. No. 5,705,577 for general process conditions.

When a solid supported catalyst is used for the conversion, a slurry polymerization/oligomerization process generally operates in the similar temperature, pressure and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge or settlement. The fluid is then distilled to remove solvent, any unreacted components and light product. A portion or all of the solvent and unreacted component or light components can be recycled for reuse.

If the catalyst used is un-supported, is a solution catalyst, when the reaction is complete or when the product is withdrawn from the reactor (such as in a CSTR), the product may still contain soluble, suspended or mixed catalyst system components. These components are preferably deactivated or removed. Any of the usual catalyst deactivation methods or aqueous wash methods can be used to remove the catalyst system component. Typically, the reaction is deactivated by addition of stoichiometric amount or excess of air, moisture, alcohol, isopropanol, etc. The mixture is then washed with dilute sodium hydroxide or with water to remove catalyst system components. The residual organic layer is then subjected to distillation to remove solvent, which can be recycled for reuse. The distillation can further remove any light reaction product from C18 and less. These light components can be used as diluent for further reaction. Or, they can be used as olefinic raw material for other chemical synthesis, as these light olefin product have vinylidene unsaturation, most suitable for further functionalization to convert in high performance fluids. Or, these light olefin products can be hydrogenated to be used as high quality paraffinic solvents.

Polymerization or oligomerization in absence of hydrogen is also advantageous to provide polymers or oligomers with high degree of unsaturated double bonds. These double bonds can be easily converted into functionalized fluids with multiple performance features. Examples for converting these polymers with MW greater than 300 can be found in preparation of ashless dispersants, by reacting the polymers with maleic anhydride to give PAO-succinic anhydride which can then reacted with amines, alcohols, polyether alcohols to convert into dispersants. Examples for such conversion can be found in the book "Lubricant Additives: Chemistry and Application," ed. By Leslie R. Rudnick, p. 143-170.

Desirably, in the process of the present disclosure, due to the structure features of the metallocene compound, the polymerization reaction mixture existing the polymerization reactor typically comprises residual olefin monomer feed, oligomers including vinylidenes, tri-substituted vinylenes, optionally 1,2-di-substituted vinylenes, and optionally vinyls, optionally solvents, and components derived from the catalyst system.

The polymerization reaction mixture is then typically quenched by the addition of a quenching agent such as water, $CO_2$, methanol, ethanol, mixtures thereof, and the like. Subsequently, the polymerization reaction mixture is separated to remove the residual monomer, which can be recycled to the polymerization reactor. Monomer removal can be carried out by means such as flashing under vacuum, distillation, or extraction. The resultant mixture is an unsaturated PAO material comprising vinylidenes, tri-substituted vinylenes, optionally 1,2-di-substituted vinylenes, and optionally vinyls.

The unsaturated PAO material desirably comprises vinylidenes and tri-substituted vinylenes at a high concentration, desirably in the range from c1 to c2 mol % in total, where c1 and c2 can be, independently, 50, 55, 60, 65, 70, 75, 80, 85, 90, based on the total moles of vinyls, vinylidenes, 1,2-di-substituted vinylenes, and tri-substituted vinylenes, as long as c1<c2. Preferably, c1=60, c2=85. More preferably, c1=70, c2=80. It is known that vinylidenes and tri-substituted vinylenes are more reactive than 1,2-di-substituted vinylenes when reacted with many functionalizing agents. Thus, the high concentration of vinylidenes and tri-substituted vinylenes in the unsaturated PAO material of the present disclosure is particularly advantageous if the unsaturated PAO material is used as intermediates for making functionalized olefins.

The unsaturated PAO material desirably contains 1,2-di-substituted vinylenes at a low concentration in the range from c5 to c6 mol %, based on the total moles of vinyls, vinylidenes, 1,2-di-substituted vinylenes, and tri-substituted vinylenes in the unsaturated PAO material, where c5 and c6 can be 0, 0.5, 1, 2, 3, 4, 5, 6, 7, 8, 9, 10, 11, 15, 20, 25, 30, 35, 40, as long as c5<c6. Preferably, c5=0, c6=30. More preferably, c5=0, c6=20.

Between the vinylidenes and tri-substituted vinylenes in the unsaturated PAO material of the present disclosure, vinylidenes tend to have a higher concentration than the tri-substituted vinylenes. Desirably, in the unsaturated PAO material of the present disclosure, the concentration of vinylidenes can range from c3 to c4 mol %, based on the total moles of the vinyls, vinylidenes, 1,2-di-substituted vinylenes, and tri-substituted vinylenes, where c3 and c4 can be, independently, 45, 50, 55, 60, 65, 70, 75, 80, 85, 90, as long as c3<c4. Preferably, c3=50, c4=75. More preferably, c3=55, c4=70.

The unsaturated PAO material obtained immediately after monomer removal can contain dimers, trimers, tetramers, pentamers, and even oligomers with a higher degree of polymerization. Extraction or fractionation may be carried out to separate the product into multiple fractions with differing boiling point ranges, corresponding to differing molecular weight range and differing degree of polymerization. For example, dimers can be separated out as a low-viscosity, low boiling point fraction as one grade of product, and the residual material may be used as another product grade of the unsaturated PAO material.

V.4 Hydrogenation

At least a portion of the unsaturated PAO material can be hydrogenated to obtain an at least partly saturated PAO material. The unsaturated PAO material is preferably treated to reduce heteroatom-containing compounds to less than 600 ppm, and then contacted with hydrogen and a hydrogenation catalyst to produce a at least partly saturated, hydrogenated PAO material. The hydrogenated PAO material desirably has a bromine number less than 2.0, more desirably less than 1.8. Preferably the hydrogenation catalyst is selected from the group consisting of supported Group 7, 8, 9, and 10 metals. Preferably, the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on kieselguhr, or platinum or palladium supported on alumina, or cobalt-molybdenum supported on alumina. Preferably, a high nickel content catalyst, such as 60% Ni on Kieselguhr catalyst can be used, or a supported catalyst with high amount of Co—Mo loading. Alternately, the hydrogenation catalyst can be nickel supported on kieselguhr, silica, alumina, clay or silica-alumina.

Preferably, the polyalpha-olefin is contacted with hydrogen and a hydrogenation catalyst at a temperature from 25 to 350° C., preferably 100 to 300° C. Preferably, the polyalpha-olefin is contacted with hydrogen and a hydrogenation catalyst for a time period from 5 minutes to 100 hours, preferably from 5 minutes to 24 hours. Preferably, the unsaturated PAO material is contacted with hydrogen and a hydrogenation catalyst at a hydrogen pressure of from 25 psi to 2500 psi, preferably from 100 to 2000 psi. Further information on hydrogenation of unsaturated PAO materials can be found in U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994).

This hydrogenation process can be accomplished in a slurry reactor in a batch operation or in a continuous stirred tank reactor (CSTR), where the catalyst in 0.001 wt % to 20 wt % of the unsaturated PAO feed or preferably 0.01 to 10 wt %, hydrogen and the uPAOs are continuously added to the reactor to allow for certain residence time, usually 5 minutes to 10 hours to allow substantially complete hydrogenation of the unsaturated olefins. The amount of catalyst added is usually very small just to compensate for the catalyst deactivation. The catalyst and hydrogenated PAO can be continuously withdrawn from the reactor. The product mixture can be filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst can be packed inside a tubular reactor and heated to reactor temperature. Hydrogen and PAO feed can be fed through the reactor simultaneously from the top or bottom or counter-current-wise to maximize the contact between hydrogen, PAO and catalyst and to allow best heat management. The feed rate of the PAO and hydrogen are adjusted to give proper residence time to allow complete hydrogenation of the unsaturated PAOs in the feed. The hydrogenated PAO fluid can be used as is or further distilled or fractionated to give the right component, if necessary. Usually, the finished hydrogenated PAO material can have a bromine number less than 2.

The present disclosure is further illustrated by the following non-limiting examples.

Properties of the uPAO or hydrogenated PAO materials such as KV40, KV100, molecular weight distribution, polydispersity, viscosity index, and the like, are determined by using methods described above. In all data tables presented herein, "Cat Loading" means catalyst loading expressed in terms of grams of feed per gram of metallocene compound used; "Time" means residence time; "C6" means 1-hexene; "C8" means 1-octene; "C10" means 1-decene; "C12" means 1-dodecene; "C14" means 1-tetradecene; "1,2-disubs" means 1,2-disubstituted vinylenes; "trisubs" means trisubstituted vinylenes; and "N/D" means not determined.

Example 1

A mixture of 1-octene and 1-dodecene at mass ratio of 4/1 was oligomerized in a continuous stirred-tank reactor in the presence of a metallocene catalyst system comprising rac-dimethylsilyl bis(4,5,6,7-tetrahydroindenyl)zirconium dichloride (z-metallocene), tri-n-octyl aluminum (TNOA) and N,N-dimethylanilinium tetrakis(penta-fluorophenyl) borate (DTFB, or D4). The reaction mixture effluent was then quenched, filtered, and distilled under vacuum to remove monomers and dimers to obtain an uPAO mixture having a KV100 of 64.2 cSt.

Example 2

Similar to Example 1, except the oligomerization occurred at a temperature lower than that in Example 1, an uPAO material having a KV100 of 160.5 cSt was obtained.

Example 3

Similar to Example 1, except that the 1-octene and 1-dodecene were used at a mass ratio of about 70/30, and the oligomerization occurred at an even lower temperature than in Example 2 and a higher concentration of the z-metallocene compound, an uPAO material having a KV100 of 297.3 cSt was obtained.

Compositions and properties of these products of Example Nos. 1, 2, and 3 are included in TABLE II below.

TABLE II

|  |  | Example No. | | |
|---|---|---|---|---|
|  |  | 1 | 2 | 3 |
| KV100 (cSt) | | 64.2 | 160.5 | 297.3 |
| Composition (mol %) | Vinylidenes | 62.81 | 52.76 | 35.14 |
|  | 1,2-Disubs | 22.77 | 30.67 | 45.05 |
|  | Trisubs | 14.42 | 16.56 | 19.82 |
|  | Vinyls | 0.00 | 0.00 | 0.00 |
| Tacticity (mol %) | (m,m)-triads | 89.21 | 91.35 | 92.39 |
|  | (m,r)-triads | 6.08 | 4.74 | 3.99 |
|  | (r,r)-triads | 4.71 | 3.91 | 3.62 |
| Molecular Weight | Mn | 2778 | 4163 | 5896 |
|  | Mw | 4024 | 6648 | 10363 |
|  | PDI | 1.45 | 1.6 | 1.76 |

As is clear from the data in TABLE II, the higher the viscosity (KV100) of the unsaturated PAO material, the higher the average molecular weight, and the higher the PDI thereof. This is because the larger the average molecular weight of a polymer material having substantially the same structure, the higher its melting point tends to be, and the more difficult it is to flow at a given temperature. In addition, when the same catalyst system is used, typically the higher the average molecular weight of the polymer, the broader the distribution of the molecular weight of the polymer material will be, resulting in a larger PDI thereof. However, the unsaturated PAO material of Example Nos. 1, 2, and 3 above are considered as PAOs with relatively small PDI at their respective average molecular weights.

Example Nos. 1, 2, and 3 also showed slightly different compositions in terms of distribution of olefin types in the mixture, even though the same monomer mixture and the same metallocene-compound-based catalyst system was used for fabricating them. All three examples demonstrated high isotacticity characterized by a molar concentration of (m,m)-triads of greater than 85 mol %. All three examples demonstrated exceedingly low concentrations of vinyls. As the average molecular weight increases, the KV100 increases, and the concentration of vinylidenes decreases, and both of the concentrations of 1,2-di-substituted vinylenes and tri-substituted vinylenes increase.

With respect to Example No. 1, the uPAO comprises a great majority of terminal olefins. The highly reactive terminal C=C bond can react with many different types of chemical agents, such as organic halides, thiols, anhydrides, and the like, forming various types of functionalized PAOs, in the presence or in the absence of a catalyst. Typically, such terminal C=Cs bonds are present close to an end of the longest carbon backbone of the PAO molecule. Therefore, the functional groups thus introduced into the PAO molecule via reaction with a functional group with the double bond tend to attach to a carbon close to an end of the longest carbon backbone of the PAO molecule. The functionalized PAO molecule could therefore possess two distinctively differing ends, imparting surfactant-like properties thereto.

With respect to Example No. 3, however, a great majority of the olefins in the mixture are internal olefins (1,2-di-substituted and tri-substituted vinylenes). This suggest that, for the metallocene-catalyzed PAOs, the chain termination mechanism of large unsaturated PAO molecules during the polymerization process may differ from that of small unsaturated PAO molecules, and/or the fabrication process resulted in isomerization of the vinylidenes resulting in the conversion thereof to 1,2-di-substituted vinylenes and/or tri-substituted vinylenes. Regardless of the mechanism creating the higher concentrations of internal olefins (di- and tri-substituted vinylenes), it is believed that the C=C bond is nonetheless located at close to one end of the longest carbon backbone of the PAO molecule. Without intending to be bound by a particular theory, it is believed that the metallocene-catalyst used in all Example Nos. 1, 2, and 3 do not propagate the polymerization from an internal olefin.

It is believed that such internal olefins (i.e., the vinylenes) are not as reactive as terminal olefins (such as the PAO of Example No. 1) with respect to many typical chemical agents under the same reaction conditions. Therefore, to further functionalize the high molecular weight, high viscosity unsaturated PAO materials of Example Nos. 2 and 3, one may need to utilize one or more of (i) a catalyst system capable of activating an internal C=C bond, (ii) chemicals more selective toward internal C=C bonds, and (iii) reacting conditions (such as partial pressure, concentration, temperature, residence time, and the like) more favorable for internal olefins. However, as indicated above, given the proximity of C=C bonds to an end of the PAO molecule, even in the internal olefins, one can expect that a functional group attached to one of the two carbon atoms as a result of functionalization of the C=C bond would likewise be located close to an end of the PAO molecule, resulting in a PAO molecule with potentially distinctly differing two ends exhibiting properties and behavior interesting for many uses, such as detergents, biologically active vectors, and the like.

Examples 4-11

In Examples 4-10, pure 1-decene was oligomerized in a continuous stirred-tank reactor in the presence of a metallocene catalyst system comprising the z-metallocene used in Examples 1, 2, and 3, tri-n-octylaluminum ("TNOA") and N,N-dimethylanilinium tetrakis(penta-fluorophenyl) borate ("D4") at various catalyst loadings. The reaction mixture effluent was quenched, filtered, and distilled under vacuum to remove monomers and dimers to obtain an uPAO mixture having various KV100. Example 11 was carried out in substantially the same manner except in a semi-batch reactor. The uPAO materials were then characterized by $^{13}$C NMR to determine the distribution of different types of olefins (i.e., vinylidenes, vinyls, tri-substituted vinylenes, and 1,2-disubstituted vinylenes).

The catalyst loadings, temperatures of the reaction mixture in the reactor, measured KV100 in cSt, and the distribution of the olefins in the uPAO materials in mole percentages are provided in TABLE III below.

TABLE III

|  | Example No. | | | | | | | |
|---|---|---|---|---|---|---|---|---|
|  | 4 | 5 | 6 | 7 | 8 | 9 | 10 | 11 |
| Cat Loading | 32392 | 84487 | 85367 | 84487 | 84487 | 84487 | 170733 | 14200 |
| Temp (° C.) | 103 | 71 | 58 | 52 | 46 | 40 | 40 | 135 |
| KV100 (cSt) | 17.08 | 61.31 | 146.2 | 214.9 | 309.2 | 419.4 | 509.3 | 3.33 |

TABLE III-continued

|  | Example No. | | | | | | | |
| --- | --- | --- | --- | --- | --- | --- | --- | --- |
|  | 4 | 5 | 6 | 7 | 8 | 9 | 10 | 11 |
| 1,2-disubs (%) | 14.4 | 25.7 | 39.2 | 44.2 | 42.4 | 55.2 | 54.6 | 4.2 |
| Trisubs (%) | 31.9 | 14.4 | 16.5 | 15.0 | 22.0 | 16.6 | 15.3 | 13.5 |
| Vinyls (%) | 0.6 | 0 | 0.8 | 4.0 | 6.8 | 4.4 | 7.7 | 0.1 |
| Vinylidenes (%) | 53.1 | 59.8 | 43.5 | 36.7 | 28.8 | 23.8 | 22.4 | 82.1 |

Examples 12-20

For these examples, solution polymerizations were performed using a high-throughput robotic system manufactured by Symyx Technologies (now Unchained Labs, having an office in Pleasanton, Calif. 94566, U.S.A.). The reactions took place in parallel in reaction wells lined with disposable glass inserts and equipped with stirring bars. Stock solutions of rac-dimethylsilyl bis(4,5,6,7-tetrahydroindenyl)zirconium dimethyl (mez-metallocene), the same or different in quantities in each example as appropriate, and activator in toluene were added separately to an isohexane reaction solvent containing a specific amount of tri-n-octylaluminum (TNOA). Monomers were then added and the reaction was allowed to run for 1 hour. The total volume of monomers, solvent, metallocene, activator, and scavenger was maintained at 5.1 mL. Upon completion of the oligomerization, the reactions were quenched with $CO_2$ addition and volatiles were flashed off under reduced pressure at 70° C. Residual unsaturated PAO materials were then characterized for the distribution of the olefins in the product, and their respective physical properties such as KV100.

The composition (in micromoles) of the materials charged into the reactor was as follows:

| Component | Quantity (micro mole) |
| --- | --- |
| 1-Decene | 10565.3 |
| Isohexane | 21051.5 |
| TNOA | 0.6 |
| Toluene | 3754 |
| D4 or D9 co-catalyst | 0.08 |
| Mez-metallocene | 0.08 |

Monomer of 1-Decene (comprising at least 94% 1-decene) was purchased from Aldrich Chemical (www.sigmaaldrich.com) and purified by passing through a basic alumina column and dried over 3 Å molecular sieves. Dimethylanilinium tetrakis(perfluorophenylborate) (D4) and dimethylanilinium tetrakis(perfluoronaphthylborate) (D9) were purchased from Albemarle Corporation having an address in Pasadena, Tex., U.S.A., and used as received. Reaction solvents were purchased as anhydrous versions from Aldrich Chemical and dried with activated 3 Å molecular sieves for at least 24 hours prior to use. Methylalumoxane (MAO) was purchased from Albemarle Corporation as a 30 wt % solution in toluene.

For reactions with MAO, the composition in the reactor (in micromoles) was:

| Component | Quantity (micro mole) |
| --- | --- |
| 1-Decene | 10565.34 |
| Isohexane | 20663.73 |
| MAO | 25.76 |

-continued

| Component | Quantity (micro mole) |
| --- | --- |
| Toluene | 4213.82 |
| Mez-metallocene | 0.08. |

Reaction conditions including the activator identities, oligomerization temperatures, and distribution of the olefins in the products are provided in TABLE IV below.

TABLE IV

|  | Example | | | | | | | | |
| --- | --- | --- | --- | --- | --- | --- | --- | --- | --- |
|  | 12 | 13 | 14 | 15 | 16 | 17 | 18 | 19 | 20 |
| Activator | D9 | MAO | D4 | D9 | MAO | D4 | D9 | MAO | D4 |
| Temp (° C.) | 60 | 60 | 60 | 85 | 85 | 85 | 110 | 110 | 110 |
| 1,2-Disubs (%) | 20.2 | 26 | 21 | 15.6 | 16 | 11 | 12.4 | 12 | 7 |
| Trisubs (%) | 35.0 | 5 | 7 | 28.9 | 9 | 11 | 33.5 | 12 | 13 |
| Vinyls (%) | — | — | — | — | — | — | — | — | — |
| Vinylidenes (%) | 44.8 | 69 | 73 | 55.6 | 75 | 79 | 54.1 | 75 | 80 |

Examples 21 to 28

Various mixtures of 1-hexene, 1-decene, and 1-tetradecene, and various mixtures of 1-octene and 1-dodecene were oligomerized in a continuous stirred-tank reactor in the presence of a metallocene catalyst system comprising the z-metallocene of Example 1, tri-n-octyl aluminum (TNOA) and N,N-dimethylanilinium tetrakis(penta-fluorophenyl) borate (DTFB, or D4), at various residence time and reaction temperatures. The reaction mixture effluent was then quenched, filtered, and distilled under vacuum to remove monomers and dimers to obtain an uPAO mixture having various KV100. The uPAO mixtures of Examples 21, 22, and 23 were subsequently hydrogenated by contacting with hydrogen in the presence of a hydrogenation catalyst to remove substantially all of the unsaturated C=C bonds in the molecules. Data are reported in TABLE V below. With regard to Examples 21, 22, and 23, the reported KV40, KV100 and VI values are those of the hydrogenated PAO, not the uPAO mixtures. While the olefin distribution data for the uPAO mixtures of Examples 21, 22, and 23 were not determined, it is believed they are similar to those of Examples 24-28 due to the same catalyst system used.

TABLE V

| | | Example | | | | | | | |
|---|---|---|---|---|---|---|---|---|---|
| | | 21 | 22 | 23 | 24 | 25 | 26 | 27 | 28 |
| Activator | | D4 | D4 | D4 | D4 | D4 | D4 | D4 | D4 |
| Temp (° C.) | | 58.2 | 58 | 58.5 | 74 | 73.5 | 90 | 75 | 60 |
| Cat Loading | | 84500 | 84500 | 84500 | 82000 | 97000 | 230000 | 84600 | 17400 |
| Time (hour) | | 3 | 3 | 3 | 3 | 3 | 2.25 | 3 | 5 |
| Feed (wt %) | C6 | 20 | 17 | 15 | 20 | 17 | — | — | — |
| | C8 | — | — | — | — | — | 80 | 80 | 80 |
| | C10 | 65 | 68 | 70 | 65 | 68 | — | — | — |
| | C12 | — | — | — | — | — | 20 | 20 | 20 |
| | C14 | 15 | 15 | 15 | 15 | 15 | — | — | — |
| 1,2-Disubs (%) | | N/D | N/D | N/D | 23.4 | 22.9 | 20.93 | 22.02 | 24.74 |
| Trisubs (%) | | N/D | N/D | N/D | 23.9 | 13.8 | 12.59 | 14.72 | 17.56 |
| Vinyls (%) | | N/D | N/D | N/D | 0 | 3.7 | 0.75 | 0 | 0 |
| Vinylidenes (%) | | N/D | N/D | N/D | 52.7 | 59.6 | 65.73 | 63.26 | 57.7 |
| KV40 (cSt) | | 1694 | 1682 | 1664 | 583.2 | 593.5 | 516.9 | 556 | 619.2 |
| KV100 (cSt) | | 160.5 | 160.2 | 160.4 | 63.37 | 65.11 | 58.15 | 62.21 | 68.1 |
| VI | | 211 | 211 | 212.9 | 181.3 | 184 | 182 | 184 | 186.1 |

The invention claimed is:

1. An unsaturated polyalpha-olefin material comprising an olefin mixture of vinylidene olefins, 1,2-di-substituted vinylene olefins, and tri-substituted vinylene olefins, the olefin mixture having:
   (I) an isotacticity of at least 50%, expressed as the mole percentage of (m,m)-triads as measured by using $^{13}C$ NMR;
   (II) a number-average molecular weight from 100 to 10,000;
   (III) a polydispersity index in the range from 1.0 to 2.0;
   (IV) a kinematic viscosity at 100° C. in the range from 20 to 1000 cSt; and
   (V) based on the total moles of the vinylidene olefins, 1,2-di-substituted vinylene olefins, and tri-substituted vinylene olefins:
   a concentration of the vinylidene olefins in the range from 3 to 80 mol %;
   a concentration of the 1,2-di-substituted vinylene olefins in the range from 10-70 mol %; and
   a concentration of the tri-substituted vinylene olefins in the range from 5 to 60 mol %.

2. The unsaturated polyalpha-olefin material of claim 1, wherein the olefin mixture has at least one of the following (V.1), (V.2), and (V.3), based on the total moles of the vinylidene olefins, 1,2-di-substituted vinylene olefins, and tri-substituted vinylene olefins:
   (V.1) a concentration of the vinylidene olefins of [a] mol %, where $a1 \leq [a] \leq a2$;
   (V.2) a concentration of the 1,2-di-substituted vinylene olefins of [b] mol %, where $b1 \leq [b] \leq b2$; and
   (V.3) a concentration of the tri-substituted vinylene olefins of [c] mol %, where $c1 \leq [c] \leq c2$;
   where:

$a1 = -0.06*V + 26.9$;

$a2 = -0.06*V + 83.9$;

$b1 = 0.04*V + 12.9$;

$b2 = 0.12*V + 29.1$;

$c1 = 0.01*V + 7.6$; and $c2 = -0.04*V + 62.1$;

wherein V is the kinematic viscosity at 100° C. of the olefin mixture of the vinylidene olefins, 1,2-di-substituted vinylene olefins, and tri-substituted vinylene olefins.

3. The unsaturated polyalpha-olefin material of claim 2, wherein at least one of the following is met:

$a3 \leq [a] \leq a4$;

$b3 \leq [b] \leq b4$; and $c3 \leq [c] \leq c4$;

where:

$a3 = -0.09*V + 55.2$;

$a4 = -0.08*V + 76.8$;

$b3 = 0.09*V + 14.4$;

$b4 = 0.09*V + 23.4$;

$c3 = 0.01*V + 11.1$; and $c4 = -0.02*V + 30.3$.

4. The unsaturated polyalpha-olefin material of claim 1, wherein the unsaturated polyalpha-olefin material has:
   (VI) a total concentration of the vinylidene olefins, the 1,2-di-substituted vinylene olefins, and the tri-substituted vinylene olefins of at least 50 wt %, based on the total weight of the unsaturated polyalpha-olefin material.

5. The unsaturated polyalpha-olefin material of claim 1, wherein the unsaturated polyalpha-olefin material has:
   (VI) a total concentration of the vinylidene olefins, the 1,2-di-substituted vinylene olefins, and the tri-substituted vinylene olefins of at least 80 wt %, based on the total weight of the unsaturated polyalpha-olefin material.

6. The polyalpha-olefin of claim 1, wherein the olefin mixture has an isotacticity of at least 60%.

7. The unsaturated polyalpha-olefin material of claim 2, wherein the olefin mixture of the vinylidene olefins, the 1,2-di-substituted vinylene olefins, and the tri-substituted vinylene olefins has a kinematic viscosity at 100° C. in the range from 30 to 100 cSt, and a1=21; a2=82; b1=14; b2=41; c1=8; and c2=61.

8. The unsaturated polyalpha-olefin material of claim 2, wherein the olefin mixture of the vinylidene olefins, the 1,2-di-substituted vinylene olefins, and the tri-substituted vinylene olefins has a kinematic viscosity at 100° C. in the range from 120 to 180 cSt, and a1=16; a2=77; b1=18; b2=51; c1=9; and c2=57.

9. The unsaturated polyalpha-olefin material of claim 2, wherein the olefin mixture of the vinylidene olefins, the 1,2-di-substituted vinylene olefins, and the tri-substituted vinylene olefins has a kinematic viscosity at 100° C. in the range from 270 to 330 cSt, and a1=7; a2=68; b1=23; b2=69; c1=10; and c2=51.

10. The unsaturated polyalpha-olefin material of claim 1, wherein the olefin mixture is made by using a metallocene-compound based catalyst system.

11. The unsaturated polyalpha-olefin material of claim 1, wherein the olefin mixture consists of structural units derived from one or more of C6-C30 linear alpha-olefins.

12. The unsaturated polyalpha-olefin material of claim 1, wherein the olefin mixture consists of structural units derived from one or more of C8-C16 linear alpha-olefins.

13. The unsaturated polyalpha-olefin material of claim 1, wherein the olefin mixture consists of structural units derived from one or more of C8, C10, C12, and C14 linear alpha-olefins.

14. The unsaturated polyalpha-olefin material of claim 1, wherein the olefin mixture consists of structural units derived from a mixture of C8 and C12 linear alpha-olefins.

15. The unsaturated polyalpha-olefin material of claim 1, wherein the olefin mixture has a polydispersity index in a range from 1.2 to 1.9.

16. The unsaturated polyalpha-olefin material of claim 1, further comprising saturated polyalpha-olefins at a total concentration of no greater than 20 wt %, based on the total weight of the unsaturated polyalpha-olefin material.

17. The unsaturated polyalpha-olefin material of claim 1, having a Bromine number in the range from 2.0 to 8.0.

18. The unsaturated polyalpha-olefin material of claim 1, comprising vinyls at a total concentration of no greater than 5.0 wt %, based on the total weight of the olefins in the unsaturated polyalpha-olefin material.

19. The unsaturated polyalpha-olefin material of claim 1, having a total concentration of the vinylidene olefins higher than the total concentration of the 1,2-di-substituted vinylene olefins and the tri-substituted vinylene olefins.

20. The unsaturated polyalpha-olefin material of claim 1, having a total concentration of the vinylidene olefins lower than the total concentration of the 1,2-di-substituted vinylene olefins and the tri-substituted vinylene olefins.

21. The unsaturated polyalpha-olefin material of claim 1, having a total concentration of the vinylidene olefins lower than the total concentration of the 1,2-di-substituted vinylene olefins.

* * * * *